US006913906B2

(12) United States Patent
Bolen et al.

(10) Patent No.: US 6,913,906 B2
(45) Date of Patent: Jul. 5, 2005

(54) FLAVOR ACTIVE MODIFIED THAUMATIN AND MONELLIN AND METHODS FOR THEIR PRODUCTION AND USE

(76) Inventors: Paul L. Bolen, 821 Buchanan Blvd., Red Bank, NJ (US) 07701; Paul L. Cihak, 31 Oakwood Rd., Leonardo, NJ (US) 07737; Lewis G. Scharpf, Jr., 35 Lewis Point Rd., Fair Haven, NJ (US) 07704; Kevin P. Miller, 50 Farm Rd., Middletown, NJ (US) 07748; Nicolas Kossiakoff, 8 Clos de la Chauderie, rue Chaude, 78240 Chambourcy (FR); Regina D. Hawn, 222 Main St., Matawan, NJ (US) 07747

( * ) Notice: Subject to any disclaimer, the term of this patent is extended or adjusted under 35 U.S.C. 154(b) by 371 days.

(21) Appl. No.: 10/175,389

(22) Filed: Jun. 20, 2002

(65) Prior Publication Data

US 2003/0050445 A1 Mar. 13, 2003

Related U.S. Application Data

(62) Division of application No. 09/224,514, filed on May 6, 1999, now Pat. No. 6,420,527.

(51) Int. Cl.[7] .............................................. C12P 21/06
(52) U.S. Cl. ......................... 435/69.1; 435/6; 435/7.1; 435/252.3; 435/320.1; 435/325; 536/23.1; 536/23.5; 536/24.3; 530/350
(58) Field of Search ........................... 435/69.1, 6, 7.1, 435/252.3, 320.1, 325; 536/23.1, 23.5, 24.3; 530/350

(56) References Cited

U.S. PATENT DOCUMENTS 5,221,624 A * 6/1993 Blair et al. ............ 435/252.33
5,670,339 A   9/1997 Kim et al. .................. 435/69.1

FOREIGN PATENT DOCUMENTS

EP          832972 A2     1/1998

OTHER PUBLICATIONS

Cagan, R.H., Experimentia 40: 843–844 (1984).
De Vos, A.M., et al, PINAS USA 82: 1406–1409 (1985).
Iijima, H., Baiosaiensu to Indasutori 53: 963–966 (1995).
Iyengar, R.B., Eur. J. Biochem. 96: 193–204 (1979).
Murzin, A.G. J., Mol. Biol. 230:289 (1993).
Slootstra, J.W., et al, Chemical Senses 20: 535–543 (1995).
Staff Report, Food Technology, Jan., 1996, 75–75.
Suami, T., et al, Food Chemistry 56: 275–281 (1996).
Tamura, M.T., et al, Agric. Biol. Chem. 53: 319–325 (1989).
Verrips, C.T., PLANT Microb. Biotechnol. Res. Ser., 1:219:234 (1992).
Yamasaki, Y. & Maekawa, K., Agric. Biol. Chem. 42:1761–1765.

Aguilar O.M., et al (1987), Nitrogen Fixation protein–*Rhizobium meliloti, J. Bacteriol*, 169:5393–5400, C28379NBRF.
Akusjarvi G., et al (1981), Hexon protein–Human adenovirus 2, *Nucleic Acids Res.*, 9:1–17, HXAD2BNRF.
Alin P., et al (1989), Gluthathione transferase 8, cytosolic–Rat, *Biochem.J.*, 261:531–539, XURT8CNBRF.
Allison L.A., et al (1985), DNA–directed RNA polymerase II 215K polypeptide–Yeast (*Saccharomyces cerevisiae*), *Cell*, 42:599–610, RNBY2LNBRF.
Aoki I., et al; (1991). Eosinophil granule major basic protein I precursor–Guinea pig, *FEBS Lett.*, 279:330–334, S13625NBRF.
Aoki I., et al (1991), Eosinophil granule major basic protein 2 precursor–Guinea pig, *FEBS Lett.*, 282:56–60, S15102NBRF.
Au–Young J., et al (1990), Chitin synthase–Imperfect fungus (*Candida albicans*), *Mol .Microbiol.*, 4:197–207, S11808NBRF.
Baer R., et al (1984), BRRF2 protein–Epstein–Barr virus (strain B95–8), *Nature*, 310:207–211,. QQBE3ONBRF.
Begg G.S., et al (1978), Connective–tissue activating peptide III–Human, *Proc.Natl.Acad.Sci U.S.A. Biochemistry*, 80:765–769, TGHUNBRF.
Benfield P.A., et al (1984), Creatine Kinase M chain–Rat, *J.Biol.Chem.*, 259:14979–14984 KIRTCMNBRF.
Benfield P.A., et al (1988), Creatine kinase (CK)–Rat, *Gene*, 63:227–243, JT0277NBRF.
Buskin J.N., et al (1985), Creatine kinase M chain–Mouse, *J.Mol.Evol.*, 22:334–341, A23590NBRF.
Calabrese L., et al (1989), Superoxide dismutase (Cu–Zn) Blue shark, *FEBS Lett*, 50:49–52, S04623NBRF.
Citron, B.A., et al (1984), Galactokinase–Yeast (*Saccharomyces cerevisiae*), *J.Bacteriol.*, 158:269–278, KIBYGGN-BRF.
Dawson, P.A., et al (1989), Oxysterol–binding protein–Rabbit, *J.Biol.Chem.*, 264–16798–16803, A34404NBRF.
Ghosh, S., et al (1990), Transcription factor NF–kappaB–Mouse, *Cell*, 62:1019–1029, ?A35697NBRF.
Gitt, M.A., et al (1985), DNA–directed RNA polymerase sigma chain–*Bacillus subtilits, J.Biol.Chem.*, 20:7178–7185, A22626NBRF.
Gustafson, G., et al (1989), Alpha–a protein–Barley stripe mosaic virus, *Virology*, 170:370–377, PAVBBSNBRF.
Haas, R.C., et al (1990), Creatine kinase precursor, sarcomere–specific, mitochondrial–Human, *J.Biol.Chem.*, 265:6921–6927, A35756NBRF.
Helfman, D.M., et al (1985), Tropomyosin 1, smooth muscle–Chicken, *J.Biol.Chem.*, 259:14136–14143, TMCHS1NBRF.

(Continued)

*Primary Examiner*—Jon Weber
*Assistant Examiner*—Hope A. Robinson
(74) *Attorney, Agent, or Firm*—Elizabeth M. Quirk

(57) ABSTRACT

A modified thaumatin protein and an antibody thereto are provided. Further, nucleic acid sequences and vectors capable of expressing thaumatin or monellin are provided.

12 Claims, 18 Drawing Sheets

OTHER PUBLICATIONS

Herring, B.P., et al (1990), Myosin–light–chain kinase, skeletal muscle–Rabbit, *J.Biol.Chem.*, 265:1724–1730, A35021NBRF.

Hirsch–Behnam, A, et al (1990), Hypothetical protein E1–Human papillomavirus, *Virus Res.*, 18:81–98, S15616NBRF.

Holt, J.C., et al (1986), Platelet basic protein–Human, *Biochemistry*, 25:1988–1996, A24448NBRF.

Hossle, J.P., et al (1986), B–creatine kinase protein–Chicken, *Nucleic Acids Res.*, 14:1449–1463, A24793NBRF.

Hossle, J.P., et al (1988), Creatine kinase precursor, mitochondrial–Chicken (fragment), *Biochem.Biophys.Res.Commun.*, 151:408–416, A27708NBRF.

Jofuki, K.D., et al (1989), Trypsin inhibitor Kti3+ (Kunitz)–Soybean, *Plant Cell*, 1:427–435, JQ0968NBRF.

Jornvall, H., et al (1981), Hexon protein–Human adenovirus 2, *J.Biol.Chem.*, 256:6181–6186, HXAD2NBRF.

Larimer, F.W., et al (1989), revl protein–Yeast (*Saccharomyces cerevisiae*), *J.Bacteriol.*, 171:230–237, A32240NBRF.

Lehman, L.J. et al (1990), Dinitrogenase reductase–*Rhodospirillum rubrum*, *Gene*, 95:143–147, JW0039NBRF.

Levin, D.E., et al (1990), Protein kinase 1–Yeast, *Proc.Natl.Acad.Sci.U.S.A.*, 87:8272–8276, A36474NBRF.

Lin, C.S., et al (1988).L–plastin–Human, *Mol.Cell.Biol.*, 8:4659–4668, A31559NBRF.

Mariman, E.C.M., et al (1989), Creatine kinase chain B–Human, *Nucleic Acids Res.*, 17–6385, S15935NBRF.

Mariman, E.C.M., et al (1987), Creatine kinase B chainHuman, *Genomics*, 1:126–137, A217174NBRF.

Michaels, M.L., et al (1990), Adenine glycosylase–*Escherichia coli*, *Nucleic Acids Res.*, 18:3841–3845, JQ0546BNRF.

Mukai, H, et al (1991), Calcineurin B–like protein–Rat, *Biochem.Biophys.Res.Commun.*, 179:1325–1330, JQ1232NBRF.

Nambu, J.R., et al (1986), Egg–laying horomone–1 precursor–Sea hare, *J.Neurosci*, 6:2026–2036, A26147NBRF.

Nishiya, Y., et al (1990), Neutral proteinase–*Bacillus stearothermophilus*, *J. Bacteriol*, 172:4861–4869, B36706NBRF.

Payne, R.M., et al (1991), Creatine kinase–Rat, *Biochem. Biophys.Acta.*, 1089:352–361, S17188NBRF.

Pentecost, B.T., et al (1990), Creatine kinase B chain–Rat, *Mol.Endocrinol.*, 4:1000–1010, A35682MBRF.

Perryman, M.B., et al (1986), Creatine kinase M chain–Human, *Biochem.Biophys.Res.Commun.*, 140:981–989, A26387NBRF.

Pickering, L., et al (1985), Creatine kinase B chain–Rabbit, *Proc.Natl.Acad.Sci.U.S.A.*, 82:2310–2314, KIRBCBNBRF.

Roman, D., et al (1985), Creatine kinase M chain–Dog, *Proc.Natl.Acad.Sci.U.S.A.*, 82:8394–8398, 24685NBRF.

Rupp, F, et al (1991), Agrin–Rat, *Neuron*, 6:811–823, JH0399BNRF.

Sanders, C., et al (1985), Tropomyosin 1, smooth muscle–Chicken, *J.Biol.Chem.*, 260:7264–7275, TMCHS1NBRF.

Takio, K., et al (1986), Myosin light chain kinase, skeletal muscle–Rabbit, *Biochemistry* 25:8049–8057.

Tamura, M., et al (1989), Delicious peptide–Bovine, *Agric. Biol.Chem.*, 53:319–325, JT0438NBRF.

Trask, R.V., et al (1988) Creatine kinase M chain–Human, *J.Biol.Chem.*, 263:17142–17149, NBRF.

Tsai–Wu, J.J., et al (1991), MicA protein–*Escherichia coli*, *J.Bacteriol.*, 173:1902–1910, B38535NBRF.

Zakin, M.M., et al (1983), metL bifunctional enzyme–*Escherichia coli*, *Biological Chemistry*, 258:3028–3031, DEECK2NBRF.

Kohmura, M., et al (1993), "The Sweetness Determinant Site of the Sweet Protein Monellin", *Pept.Chem. 1992, Proc.Jpn.Symp.2d*, 341–342.

Kuramitsu, R, et al (1993), "New Usage of Aspartic Acid and Glutamic Acid as Food Materials", Chapter 10.

* cited by examiner

Flavor Protein Homologies

| | |
|---|---|
| THAUMATIN | LYS-GLY-ASP-ALA-ALA-LEU-ASP-ALA |
| OCTAPEPTIDE | LYS-GLY-ASP-GLU-GLU-SER-LEU-ALA |
| MONELLIN I | LYS-GLY-TYR-GLU-TYR-GLN-LEU-TYR |

FIG. 1

Octapeptide - BMP NBRF Aligned Sequence

Sequence Range: 1 to 8

Octapeptid    KGDEE SLA

JT0438
[   32 ]      KGDEE SLA>
              ^^^^^ ^^^
Octapeptid    KGDEE SLA

A36474              560
[   24 ]      KGDEE S>
              ^^^^^ ^
Octapeptid    KGDEE S S04623              130
[   24 ]      gGDEE S>
              v^^^^ ^
Octapeptid    KGDEE S - a24448
[   22 ]      KGkEE SL>
              ^^v^^ ^^
Octapeptid    KGDEE SL

B36706              190
[   22 ]      nGDEa SL>
              v^^^v ^^
Octapeptid    KGDEE SL C28379              370
[   22 ]      lGDlE SL>
              v^^v^ ^^
Octapeptid    KGDEE SL DEPGC               60
[   22 ]      KgiEE SL>
              ^^v^^ ^^
Octapeptid    KGDEE SL S03257
[   22 ]      aGiEE SL>
              v^v^^ ^^
Octapeptid    KGDEE SL TGHU                10
[   22 ]      KgkEE SL
              ^^v^^ ^^
Octapeptid    KGDEE SL A22626              130
[   20 ]      eGDEE>
              v^^^^
Octapeptid    KGDEE A23590              80
[   20 ]      aGDEE>
              v^^^^
Octapeptid    KGDEE A24686              80
[   20]       aGDEE>
              v^^^^

FIG. 4(A)

Octapeptid - BMP NBRF Aligned Sequence

```
Octapeptid      KGDEE a24793             80
[  20  ]        aGDEE>
                v^^^^
Octapeptid      KGDEE
                        30
A25830          __EE SLA>
[  20]            ^^  ^^^
Octapeptid        EE SLA A26147            250
[  20  ]        KGDEE>
                ^^^^^
Octapeptid      KGDEE A26387             80
[  20  ]        aGDEE>
                v^^^^
Octapeptid      KGDEE A27174             80
[  20  ]        aGDEE>
                v^^^^
Octapeptid      KGDEE A27708
[  20  ]        aGDEE>
                v^^^^
Octapeptid      KGDEE A31559
[  20  ]        KGDEE>
                ^^^^^
Octapeptid      KGDEE A31793             80
[  20  ]        aGDEE>
                v^^^^
Octapeptid      KGDEE A32240
[  20  ]        __DEE SL>
                  ^^^ ^^
Octapeptid        DEE SL A34404
[  20  ]        sGDEE>
                v^^^^
Octapeptid      KGDEE A35021             30
[  20  ]        __EE SLA>
                  ^^ ^^^
Octapeptid        EE SLA A35682             80
[  20  ]        aGDEE>
                v^^^^
Octapeptid      KGDEE
```

FIG. 4(B)

Octapeptide - BMP NBRF Aligned Sequence

A35697          450
[  20 ]         _DEE SL>
                 ^^^ ^^

Octapeptid       DEE SL

A35756          110
[  20 ]         aGDEE>
                v^^^^

Octapeptid      KGDEE

B38535           270
[  20 ]         _DEE SL>
                 ^^^ ^^

Octapeptid       DEE SL

DEECK2           530
[  20 ]         _DEE SL>
                 ^^^ ^^

Octapeptid       DEE SL

HXAD2           320
[  20 ]         KGDEn SkA>
                ^^^^v ^v^

Octapeptid      KGDEE SLA

JH0399          1580
[  20 ]         KGDfv SLA>
                ^^^vv ^^^

Octapeptid      KGDEE SLA

JQ0546           270
[  20 ]         _DEE SL>
                 ^^^ ^^

Octapeptid       DEE SL

JQ0968          200
[  20 ]         KlDkE SLA>
                ^v^v^ ^^^

Octapeptid      KGDEE SLA

JQ1232          KGDEE>
[  20 ]         ^^^^^

Octapeptid      KGDEE

JT0277           80
[  20 ]         aGDEE>
                v^^^^

Octapeptid      KGDEE

JW0039          280
[  20 ]         KsDEE aLA
                ^v^^^ v^^

Octapeptid      KGDEE SLA kIBETE          170
[  20 ]         KGfEE gLA>
                ^^v^^ v^^

Octapeptid      KGDEE SLA

KIBYGG           350
[  20 ]         ___EE SLA>

FIG. 4(C)

Octapeptid - BMP NBRF Aligned Sequence

```
                              ^^ ^^^
Octapeptid           EE SLA

KIRBCB                 80
[   20  ]            aGDEE>
                     v^^^^
Octapeptid           KGDEE KIRTCM                 80
[   20  ]            aGDEE>
                     v^^^^
Octapeptid           KGDEE PAVBBS                 770
[   20  ]            ___EE SLA>
                        ^^ ^^^
Octapeptid           EE SLA QQBE30
[   20  ]            KGDEE>
                     ^^^^^
Octapeptid           KGDEE RNBY2L                 1450
[   20  ]            __DEE SL>
                       ^^^ ^^.
Octapeptid           DEE SL S11808                 200
[   20  ]            KGDEk nLA>
                     ^^^^v v^^
Octapeptid           KGDEE SLA S13625
[   20  ]            ___EE SLA>
                        ^^ ^^^
Octapeptid           EE SLA S15102
[   20  ]            ___EE SLA>
                        ^^ ^^^
Octapeptid           EE SLA S15616                 150
[   20  ]            tGDEE>
                     v^^^^
Octapeptid           KGDEE S15935                 80
[   20  ]            aGDEE>
                     v^^^^
Octapeptid           KGDEE S17188                 110
[   20  ]            aGDEE>
                     v^^^^
Octapeptid           KGDEE TMCHS1                 260
[   20  ]            ___EE SLA>
                        ^^ ^^^
Octapeptid           EE SLA
```

FIG. 4(D)

Octapeptid - BMP NBRF Aligned Sequence

```
XURT8C              120
 [   20 ]         __EE SLA>
                   ^^ ^^^
Octapeptid         EE SLA
```

FIG. 4(E)

Thaumatin YT152 Translated Sequence

Sequence Range: 1 to 621

```
            10          20          30          40
             *           *           *           *
    GCT ACC TTC GAA ATC GTT AAC AGA TGT TCT TAC ACT GTT TGG GCT GCT
     A   T   F   E   I   V   N   R   C   S   Y   T   V   W   A   A>
    ___a___a___a__TRANSLATION OF THAUMATIN YT152 [A]___a___a___a___>

50          60          70          80          90
      *           *           *           *           *
    GCT TCC AAG GGT GAC GCT GCT TTG GAC GCC GGT GGT AGA CAA TTG AAC
     A   S   K   G   D   A   A   L   D   A   G   G   R   Q   L   N>
    ___a___a___a__TRANSLATION OF THAUMATIN YT152 [A]___a___a___a___>

100         110         120         130         140
          *           *           *           *           *
    TCT GGT GAA TCC TGG ACC ATC AAC GTC GAA CCA GGT ACC AAG GGT GGT
     S   G   E   S   W   T   I   N   V   E   P   G   T   K   G   G>
    ___a___a___a__TRANSLATION OF THAUMATIN YT152 [A]___a___a___a___>

150         160         170         180         190
          *           *           *           *           *
    AAG ATC TGG GCT AGA ACC GAC TGT TAC TTC GAT GAC TCT GGT TCC GGT
     K   I   W   A   R   T   D   C   Y   F   D   D   S   G   S   G>
    ___a___a___a__TRANSLATION OF THAUMATIN YT152 [A]___a___a___a___>

200         210         220         230         240
          *           *           *           *           *
    ATC TGT AAG ACT GGT GAC TGT GGT GGT TTG TTG AGA TGT AAG AGA TTC
     I   C   K   T   G   D   C   G   G   L   L   R   C   K   R   F>
    ___a___a___a__TRANSLATION OF THAUMATIN YT152 [A]___a___a___a___>

250         260         270         280
          *           *           *           *
    GGT AGA CCA CCA ACC ACT TTG GCT GAA TTC TCT TTG AAC CAA TAC GGT
     G   R   P   P   T   T   L   A   E   F   S   L   N   Q   Y   G>
    ___a___a___a__TRANSLATION OF THAUMATIN YT152 [A]___a___a___a___>

290         300         310         320         330
     *           *           *           *           *
    AAG GAC TAC ATC GAT ATC TCC AAC ATC AAG GGT TTC AAC GTT CCA ATG
     K   D   Y   I   D   I   S   N   I   K   G   F   N   V   P   M>
    ___a___a___a__TRANSLATION OF THAUMATIN YT152 [A]___a___a___a___>

340         350         360         370         380
          *           *           *           *           *
    GAC TTC TCT CCA ACC ACT AGA GGT TGT AGA GGC GTC AGA TGT GCT GCT
     D   F   S   P   T   T   R   G   C   R   G   V   R   C   A   A>
    ___a___a___a__TRANSLATION OF THAUMATIN YT152 [A]___a___a___a___>

390         400         410         420         430
          *           *           *           *           *
    GAC ATC GTT GGT CAA TGT CCA GCT GAC CTT AAG GCT CCA GGT GGT GGT
     D   I   V   G   Q   C   P   A   D   L   K   A   P   G   G   G>
    ___a___a___a__TRANSLATION OF THAUMATIN YT152 [A]___a___a___a___>

440         450         460         470         480
          *           *           *           *           *
    TGT AAC GAC GCT TGT ACC GTT TTC CAA ACT TCC GAA TAC TGT TGT ACC
     C   N   D   A   C   T   V   F   Q   T   S   E   Y   C   C   T>
    ___a___a___a__TRANSLATION OF THAUMATIN YT152 [A]___a___a___a___>
```

FIG. 7(A)

Thaumatin YT152 Translated Sequence

```
          490         500         510         520
           *           *           *           *
ACT GGT AAG TGT GGT CCA ACC GAA TAC TCT AGA TTC TTC AAG AGA TTG
 T   G   K   C   G   P   T   E   Y   S   R   F   F   K   R   L>
___a___a___a__TRANSLATION OF THAUMATIN YT152 [A]___a___a___a___>

530         540         550         560         570
  *           *           *           *           *
.TGT CCA GAC GCT TTC TCC TAC GTC TTG GAC AAG CCA ACT ACC GTC ACT
  C   P   D   A   F   S   Y   V   L   D   K   P   T   T   V   T>
___a___a___a__TRANSLATION OF THAUMATIN YT152 [A]___a___a___a___>

580         590         600         610         620
  *           *           *           *           *
TGT CCA GGT TCT TCC AAC TAC AGA GTT ACC TTC TGT CCA ACT GCC
 C   P   G   S   S   N   Y   R   V   T   F   C   P   T   A>
___a___a__TRANSLATION OF THAUMATIN YT152 [A]___a___a___a___>
```

FIG. 7(B)

```
                                    5'- TTC AGA GAA ATT AAG GGG TAC GAA TAC CAA
                                        Phe Arg Glu Ile Lys Gly Tyr Glu Tyr Gln

TTG TAT GTT TAC GCT TCT GAC AAG CTT TTC AGA GCT GAC ATT TCT GAA GAC TAC AAG ACC
Leu Tyr Val Tyr Ala Ser Asp Lys Leu Phe Arg Ala Asp Ile Ser Glu Asp Tyr Lys Thr

CGC GGT AGA AAG TTG TTG AGA TTC AAC GGT CCA GTT CCA CCA CCA-3'
Arg Gly Arg Lys Leu Leu Arg Phe Asn Gly Pro Val Pro Pro Pro
```

FIG. 8

```
Beefy Meaty Peptide Nucleic Acid (SEQ ID NO:5) and Amino
Acid (SEQ ID NO:6) Sequences

5'-AAG-GGT-GAC-GAA-GAA-TCT-TTG-GCT-3'
   LYS-GLY-ASP-GLU-GLU-SER-LEU-ALA
```

FIG. 9

```
                                    30                                              60
5'-ATG GGA GAA TGG GAA ATT ATC GAT ATT GGA CCA TTC ACT CAA AAC TTG GGT AAG TTC GCT
   Met Gly Glu Trp Glu Ile Ile Asp Ile Gly Pro Phe Thr Gln Asn Leu Gly Lys Phe Ala 90                                             120
   GTT GAC GAA GAA AAC AAG ATT GGT CAA TAT GGT AGA TTG ACT TTC AAC AAG GTT ATT AGA
   Val Asp Glu Glu Asn Lys Ile Gly Gln Tyr Gly Arg Leu Thr Phe Asn Lys Val Ile Arg 150                                             180
   CCA TGT ATG AAG AAG ACT ATT TAC GAA AAC GAA AGA GAA ATT AAG GGG TAC GAA TAC CAA
   Pro Cys Met Lys Lys Thr Ile Tyr Glu Asn Glu Arg Glu Ile Lys Gly Tyr Glu Tyr Gln 210                                             240
   TTG TAT GTT TAC GCT TCT GAC AAG CTT TTC AGA GCT GAC ATT TCT GAA GAC TAC AAG ACC
   Leu Tyr Val Tyr Ala Ser Asp Lys Leu Phe Arg Ala Asp Ile Ser Glu Asp Tyr Lys Thr

220
   CGC GGT AGA AAG TTG TTG AGA TTC AAC GGT CCA GTT CCA CCA CCA-3'
   Arg Gly Arg Lys Leu Leu Arg Phe Asn Gly Pro Val Pro Pro Pro
```

FIG. 10

Modified 1 - 3D Translated Sequence

Sequence Range: 1 to 621

```
              10          20          30          40
       *       *    *      *    *      *    *      *    *
      GCT ACC TTC GAA ATC GTT AAC AGA TGT TCT TAC ACT GTT TGG GCT GCT
       A   T   F   E   I   V   N   R   C   S   Y   T   V   W   A   A>
      ___a___a___a__TRANSLATION OF MODIFIED 1 - 3D [A]___a___a___a___>

50          60          70          80          90
       *    *      *    *      *    *      *    *      *    *
      GCT TCC AAG GGT GAC GAG GAG TCT TTG GCC GGT GGT AGA CAA TTG AAC
       A   S   K   G   D   E   E   S   L   A   G   G   R   Q   L   N>
      ___a___a___a__TRANSLATION OF MODIFIED 1 - 3D [A]___a___a___a___>

100         110         120         130         140
       *    *      *    *      *    *      *    *      *
      TCT GGT GAA TCC TGG ACC ATC AAC GTC GAA CCA GGT ACC AAG GGT GGT
       S   G   E   S   W   T   I   N   V   E   P   G   T   K   G   G>
      ___a___a___a__TRANSLATION OF MODIFIED 1 - 3D [A]___a___a___a___>

150         160         170         180         190
       *    *      *    *      *    *      *    *      *    *
      AAG ATC TGG GCT AGA ACC GAC TGT TAC TTC GAT GAC TCT GGT TCC GGT
       K   I   W   A   R   T   D   C   Y   F   D   D   S   G   S   G>
      ___a___a___a__TRANSLATION OF MODIFIED 1 - 3D [A]___a___a___a___>

200         210         220         230         240
       *    *      *    *      *    *      *    *      *    *
      ATC TGT AAG ACT GGT GAC TGT GGT GGT TTG TTG AGA TGT AAG AGA TTC
       I   C   K   T   G   D   C   G   G   L   L   R   C   K   R   F>
      ___a___a___a__TRANSLATION OF MODIFIED 1 - 3D [A]___a___a___a___>

250         260         270         280
       *    *      *    *      *    *      *    *      *
      GGT AGA CCA CCA ACC ACT TTG GCT GAA TTC TCT TTG AAC CAA TAC GGT
       G   R   P   P   T   T   L   A   E   F   S   L   N   Q   Y   G>
      ___a___a___a__TRANSLATION OF MODIFIED 1 - 3D [A]___a___a___a___>

290         300         310         320         330
       *    *      *    *      *    *      *    *      *    *
      AAG GAC TAC ATC GAT ATC TCC AAC ATC AAG GGT TTC AAC GTT CCA ATG
       K   D   Y   I   D   I   S   N   I   K   G   F   N   V   P   M>
      ___a___a___a__TRANSLATION OF MODIFIED 1 - 3D [A]___a___a___a___>

340         350         360         370         380
       *    *      *    *      *    *      *    *      *    *
      GAC TTC TCT CCA ACC ACT AGA GGT TGT AGA GGC GTC AGA TGT GCT GCT
       D   F   S   P   T   T   R   G   C   R   G   V   R   C   A   A>
      ___a___a___a__TRANSLATION OF MODIFIED 1 - 3D [A]___a___a___a___>

390         400         410         420         430
       *    *      *    *      *    *      *    *      *    *
      GAC ATC GTT GGT CAA TGT CCA GCT GAC CTT AAG GCT CCA GGT GGT GGT
       D   I   V   G   Q   C   P   A   D   L   K   A   P   G   G   G>
      ___a___a___a__TRANSLATION OF MODIFIED 1 - 3D [A]___a___a___a___>

440         450         460         470         480
       *    *      *    *      *    *      *    *      *    *
      TGT AAC GAC GCT TGT ACC GTT TTC CAA ACT TCC GAA TAC TGT TGT ACC
       C   N   D   A   C   T   V   F   Q   T   S   E   Y   C   C   T>
      ___a___a___a__TRANSLATION OF MODIFIED 1 - 3D [A]___a___a___a___>
```

FIG. 11(A)

Modified 1 - 3D Translated Sequence

```
           490         500         510         520
            *     *     *     *     *     *     *     *     *
ACT GGT AAG TGT GGT CCA ACC GAA TAC TCT AGA TTC TTC AAG AGA TTG
 T   G   K   C   G   P   T   E   Y   S   R   F   F   K   R   L>
___a___a___a__TRANSLATION OF MODIFIED 1 - 3D [A]___a___a___a___>

530         540         550         560         570
  *     *     *     *     *     *     *     *     *     *
TGT CCA GAC GCT TTC TCC TAC GTC TTG GAC AAG CCA ACT ACC GTC ACT
 C   P   D   A   F   S   Y   V   L   D   K   P   T   T   V   T>
___a___a___a__TRANSLATION OF MODIFIED 1 - 3D [A]___a___a___a___>.

580         590         600         610         620
  *     *     *     *     *     *     *     *     *
TGT CCA GGT TCT TCC AAC TAC AGA GTT ACC TTC TGT CCA ACT GCC
 C   P   G   S   S   N   Y   R   V   T   F   C   P   T   A>
___a___a__TRANSLATION OF MODIFIED 1 - 3D [A]___a___a___a___>
```

FIG. 11(B)

SEQUENCE LISTING

<160> NUMBER OF SEQ ID NOS: 12

<210> SEQ ID NO 1
<211> LENGTH: 621
<212> TYPE: DNA
<213> ORGANISM: Bos sp.

<400> SEQUENCE: 1

```
gctaccttcg aaatcgttaa cagatgttct tacactgttt gggctgctgc ttccaagggt      60
gacgctgctt tggacgccgg tggtagacaa ttgaactctg gtgaatcctg gaccatcaac     120
gtcgaaccag gtaccaaggg tggtaagatc tgggctagaa ccgactgtta cttcgatgac     180
tctggttccg gtatctgtaa gactggtgac tgtggtggtt tgttgagatg taagagattc     240
ggtagaccac caaccacttt ggctgaattc tctttgaacc aatacggtaa ggactacatc     300
gatatctcca acatcaaggg tttcaacgtt ccaatggact tctctccaac cactagaggt     360
tgtagaggcg tcagatgtgc tgctgacatc gttggtcaat gccagctga ccttaaggct     420 ccaggtggtg gttgtaacga cgcttgtacc gttttccaaa cttccgaata ctgttgtacc     480
actggtaagt gtggtccaac cgaatactct agattcttca agagattgtg tccagacgct     540
ttctcctacg tcttggacaa gccaactacc gtcacttgtc caggttcttc caactacaga     600
gttaccttct gtccaactgc c                                               621
```

<210> SEQ ID NO 2
<211> LENGTH: 207
<212> TYPE: PRT
<213> ORGANISM: Bos sp.

<400> SEQUENCE: 2

```
Ala Thr Phe Glu Ile Val Asn Arg Cys Ser Tyr Thr Val Trp Ala Ala
 1               5                  10                  15
Ala Ser Lys Gly Asp Ala Ala Leu Asp Ala Gly Gly Arg Gln Leu Asn
            20                  25                  30
Ser Gly Glu Ser Trp Thr Ile Asn Val Glu Pro Gly Thr Lys Gly Gly
        35                  40                  45
Lys Ile Trp Ala Arg Thr Asp Cys Tyr Phe Asp Asp Ser Gly Ser Gly
 50                  55                  60
Ile Cys Lys Thr Gly Asp Cys Gly Gly Leu Leu Arg Cys Lys Arg Phe
 65                  70                  75                  80
Gly Arg Pro Pro Thr Thr Leu Ala Glu Phe Ser Leu Asn Gln Tyr Gly
                85                  90                  95
Lys Asp Tyr Ile Asp Ile Ser Asn Ile Lys Gly Phe Asn Val Pro Met
            100                 105                 110
Asp Phe Ser Pro Thr Thr Arg Gly Cys Arg Gly Val Arg Cys Ala Ala
        115                 120                 125
Asp Ile Val Gly Gln Cys Pro Ala Asp Leu Lys Ala Pro Gly Gly Gly
130                 135                 140
Cys Asn Asp Ala Cys Thr Val Phe Gln Thr Ser Glu Tyr Cys Cys Thr
145                 150                 155                 160
Thr Gly Lys Cys Gly Pro Thr Glu Tyr Ser Arg Phe Lys Arg Leu
                165                 170                 175
Cys Pro Asp Ala Phe Ser Tyr Val Leu Asp Lys Pro Thr Thr Val Thr
            180                 185                 190
Cys Pro Gly Ser Ser Asn Tyr Arg Val Thr Phe Cys Pro Thr Ala
        195                 200                 205
```

<210> SEQ ID NO 3
<211> LENGTH: 135
<212> TYPE: DNA
<213> ORGANISM: Bos sp.

<400> SEQUENCE: 3

```
ttcagagaaa ttaagggta cgaataccaa ttgtatgttt acgcttctga caagcttttc      60
agagctgaca tttctgaaga ctacaagacc cgcggtagaa agttgttgag attcaacggt     120
ccagttccac cacca                                                     135
```

<210> SEQ ID NO 4
<211> LENGTH: 45
<212> TYPE: PRT
<213> ORGANISM: Bos sp.

<400> SEQUENCE: 4

```
Phe Arg Glu Ile Lys Gly Tyr Glu Tyr Gln Leu Tyr Val Tyr Ala Ser
 1               5                  10                  15
Asp Lys Leu Phe Arg Ala Asp Ile Ser Glu Asp Tyr Lys Thr Arg Gly
            20                  25                  30
Arg Lys Leu Leu Arg Phe Asn Gly Pro Val Pro Pro
        35                  40                  45
```

<210> SEQ ID NO 5

```
<211> LENGTH: 24
<212> TYPE: DNA
<213> ORGANISM: Bos sp.

<400> SEQUENCE: 5
aagggtgacg aagaatcttt ggct                                           24

<210> SEQ ID NO 6
<211> LENGTH: 8
<212> TYPE: PRT
<213> ORGANISM: Bos sp.

<400> SEQUENCE: 6

Lys Gly Asp Glu Glu Ser Leu Ala
  1               5

<210> SEQ ID NO 7
<211> LENGTH: 285
<212> TYPE: DNA
<213> ORGANISM: Bos sp.

<400> SEQUENCE: 7
atgggagaat gggaaattat cgatattgga ccattcactc aaaacttggg taagttcgct    60
gttgacgaag aaaacaagat tggtcaatat ggtagattga ctttcaacaa ggttattaga   120
ccatgtatga agaagactat ttacgaaaac gaaagagaaa ttaagggta cgaataccaa    180 ttgtatgttt acgcttctga caagcttttc agagctgaca tttctgaaga ctacaagacc   240
cgcggtagaa agttgttgag attcaacggt ccagttccac cacca                   285

<210> SEQ ID NO 8
<211> LENGTH: 95
<212> TYPE: PRT
<213> ORGANISM: Bos sp.

<400> SEQUENCE: 8

Met Gly Glu Trp Glu Ile Ile Asp Ile Gly Pro Phe Thr Gln Asn Leu
  1               5                  10                  15

Gly Lys Phe Ala Val Asp Glu Glu Asn Lys Ile Gly Gln Tyr Gly Arg
             20                  25                  30

Leu Thr Phe Asn Lys Val Ile Arg Pro Cys Met Lys Lys Thr Ile Tyr
         35                  40                  45

Glu Asn Glu Arg Glu Ile Lys Gly Tyr Glu Tyr Gln Leu Tyr Val Tyr
     50                  55                  60

Ala Ser Asp Lys Leu Phe Arg Ala Asp Ile Ser Glu Asp Tyr Lys Thr
 65                  70                  75                  80

Arg Gly Arg Lys Leu Leu Arg Phe Asn Gly Pro Val Pro Pro
                 85                  90                  95

<210> SEQ ID NO 9
<211> LENGTH: 621
<212> TYPE: DNA
<213> ORGANISM: Artificial Sequence
<220> FEATURE:
<223> OTHER INFORMATION: Description of Artificial Sequence: Synthetic

<400> SEQUENCE: 9
gctaccttcg aaatcgttaa cagatgttct tacactgttt gggctgctgc ttccaagggt    60
gacgaggagt ctttggccgg tggtagacaa ttgaactctg gtgaatcctg gaccatcaac   120
gtcgaaccag gtaccaaggg tggtaagatc tgggctagaa ccgactgtta cttcgatgac   180
```

```
tctggttccg gtatctgtaa gactggtgac tgtggtggtt tgttgagatg taagagattc      240
cgtagaccac caaccacttt ggctgaattc tctttgaacc aatacggtaa ggactacatc      300
gatatctcca acatcaaggg tttcaacgtt ccaatggact ctctccaac cactagaggt        360 tgtagaggcg tcagatgtgc tgctgacatc gttggtcaat gtccagctga ccttaaggct      420
ccaggtggtg gttgtaacga cgcttgtacc gttttccaaa cttccgaata ctgttgtacc      480
actggtaagt gtggtccaac cgaatactct agattcttca agagattgtg tccagacgct      540
ttctcctacg tcttggacaa gccaactacc gtcacttgtc caggttcttc aactacaga       600 gttaccttct gtccaactgc c                                                621
```

<210> SEQ ID NO 10
<211> LENGTH: 207
<212> TYPE: PRT
<213> ORGANISM: Artificial Sequence
<220> FEATURE:
<223> OTHER INFORMATION: Description of Artificial Sequence: Synthetic

<400> SEQUENCE: 10

```
Ala Thr Phe Glu Ile Val Asn Arg Cys Ser Tyr Thr Val Trp Ala Ala
 1               5                  10                  15

Ala Ser Lys Gly Asp Glu Glu Ser Leu Ala Gly Gly Arg Gln Leu Asn
                20                  25                  30

Ser Gly Glu Ser Trp Thr Ile Asn Val Glu Pro Gly Thr Lys Gly Gly
            35                  40                  45

Lys Ile Trp Ala Arg Thr Asp Cys Tyr Phe Asp Ser Gly Ser Gly
         50                  55                  60

Ile Cys Lys Thr Gly Asp Cys Gly Gly Leu Leu Arg Cys Lys Arg Phe
 65                  70                  75                  80

Gly Arg Pro Pro Thr Thr Leu Ala Glu Phe Ser Leu Asn Gln Tyr Gly
                 85                  90                  95

Lys Asp Tyr Ile Asp Ile Ser Asn Ile Lys Gly Phe Asn Val Pro Met
                100                 105                 110

Asp Phe Ser Pro Thr Thr Arg Gly Cys Arg Gly Val Arg Cys Ala Ala
            115                 120                 125

Asp Ile Val Gly Gln Cys Pro Ala Asp Leu Lys Ala Pro Gly Gly Gly
        130                 135                 140

Gly Asn Asp Ala Cys Thr Val Phe Gln Thr Ser Glu Tyr Cys Cys Thr
145                 150                 155                 160

Thr Gly Lys Cys Gly Pro Thr Glu Tyr Ser Arg Phe Lys Arg Leu
                165                 170                 175

Cys Pro Asp Ala Phe Ser Tyr Val Leu Asp Lys Pro Thr Thr Val Thr
            180                 185                 190

Cys Pro Gly Ser Ser Asn Tyr Arg Val Thr Phe Cys Pro Thr Ala
        195                 200                 205
```

<210> SEQ ID NO 11
<211> LENGTH: 8
<212> TYPE: PRT
<213> ORGANISM: Bos sp.

<400> SEQUENCE: 11

```
Lys Gly Tyr Glu Tyr Gln Leu Tyr
 1               5
```

<210> SEQ ID NO 12
<211> LENGTH: 8

-continued

```
<212> TYPE: PRT
<213> ORGANISM: Bos sp.

<400> SEQUENCE: 12

Lys Gly Asp Ala Ala Leu Asp Ala
 1               5
```

FLAVOR ACTIVE MODIFIED THAUMATIN AND MONELLIN AND METHODS FOR THEIR PRODUCTION AND USE

This application is a divisional of U.S. patent application Ser. No. 09/224,514, filed on May 6, 1999, now U.S. Pat. No. 6,420,527.

Throughout this specification, various references are identified by author name in parentheses. The citation to the reference corresponding to the identified author can be found in the section entitled References Cited preceding the claims. The references in that section are hereby incorporated by reference.

BACKGROUND OF THE INVENTION

Thaumatin and monellin are flavor active and flavor enhancing proteins. Thaumatin, as shown by thaumatin II, has a wide variety of uses as a flavor enhancing agent. The octapeptide known as "delicious peptide" or "beefy meaty peptide" (BMP) is reported to enhance flavor and produces an umami and sour taste, especially in beef. Monellin is recognized as a potently sweet protein. Recent work indicates that the 19 to 26 amino acid region of thaumatin is a possible active site for sweetness determination. (Slootstra et al. 1995). Substitution of this region with other amino acid sequences, particularly those having some homology with this region of thaumatin and believed to affect taste, may alter the properties of thaumatin to provide new and useful function.

Recent work with monellin indicates that the lysine located at position 4 in the A chain is a highly likely candidate for involvement as a component of the receptor interaction site of monellin. (Suami et al. 1996). Subsitution of this region with other amino acid sequences, particularly those having some homology with this region of monellin and believed to affect taste, may alter the properties of monellin to provide new and useful function.

SUMMARY OF THE INVENTION

The present invention provides new flavor active proteins. Specifically, the new proteins are modified versions of the thaumatin and monellin proteins. In thaumatin II amino acids in the region of 19 to 26 (amino acids 19–26 of SEQ ID NO:2), which appears to be a taste active region, are replaced with other amino acid sequences. Most important is the replacement of this region with the sequences for the octapeptide known as "delicious peptide" or "beefy meaty peptide," i.e. LYS-GLY-ASP-GLU-GLU-SER-LEU-ALA SEQ ID NO:6), and the sequence that comprises the segment of protein from the fourth to the eleventh amino acid in the A chain of monellin, i.e. LYS-GLY-TYR-GLU-TYR-GLN-LEU-TYR (amino acids 4–11 of SEQ ID NO:4; SEQ ID NO:11). When four (4) of the 207 amino acids in the thaumatin b protein amino acid sequence were changed, a protein is produced that has a dramatic savory effect when evaluated with a complex salt enhancer such as L-arginine, ammonium chloride, tartaric acid, nionopotassium glutamate, or ribotide. In the presence of the salt enhancer, the new protein with the BMP sequence has a beefy, meaty, brothy impression and mouth feel.

This invention further provides a modified monellin protein, either as A and B chains or as a single joined chain, wherein the amino acids in the region of four to eleven of the A chain (or the homologous section of single chain monellin), which appears to be the taste active region, are replaced with other amino acid sequences. Most important is the replacement of this region with the sequences for the octapeptide known as "delicious peptide" or "beefy meaty peptide," i.e. LYS-GLY-ASP-GLU-GLU-SER-LEU-ALA (SEQ. ID. NO. 6), and the sequence that comprises the segment of protein from the amino acid region of 19 to 26 in thaumatin II, i.e. LYS-GLY-ASP-ALA-ALA-LEU-ASP-ALA (amino acids 19–26 of SEQ. ID. NO. 2).

This invention further provides the DNA sequences encoding the modified thaumatin and monellin proteins and for derivatives of such proteins and the DNA sequences of the derivatives. It also teaches methods for producing these proteins using genetic recombination techniques which can be used in a variety of microorganisms. According to the present invention, these proteins are expressable in yeast transformed by vectors comprising the nucleic acid sequences encoding the proteins. The microorganisms which have been transformed to express these proteins can be used to cultivate cell lines capable of producing the proteins on a large scale. Furthermore, this invention teaches the use of these proteins as flavor additives and enhancers in food.

BRIEF DESCRIPTION OF THE DRAWINGS

FIG. 1 depicts the flavor protein homologous regions of thaumatin, BMP and monellin I.

FIG. 4(A)–(E) depicts a BMP NBRF aligned sequence comparison where the corresponding NBRF number appears adjacent to the peptide compared to BMP.

FIG. 7(A)–(B) Thaumatin Nucleic Acid (SEQ ID NO:1) and (SEQ ID NO:2) Amino Acid Sequences FIG. 8 Monellin A Chain Nucleic Acid (SEQ ID NO:3) and (SEQ ID NO:4) Amino Acid Sequences FIG. 9 BMP Nucleic Acid (SEQ ID NO:5) and Amino Acid (SEQ ID NO:6) Sequences FIG. 10 Monellin Single Chain Nucleic Acid (SEQ ID NO:7) and Amino Acid (SEQ ID NO: 8) Sequences FIGS. 11(A)–(B) A Modified Thaumatin Nucleic Acid (SEQ ID NO:9) and Amino Acid (SEQ ID NO:10) Sequences

DETAILED DESCRIPTION OF THE INVENTION

Figure 2:
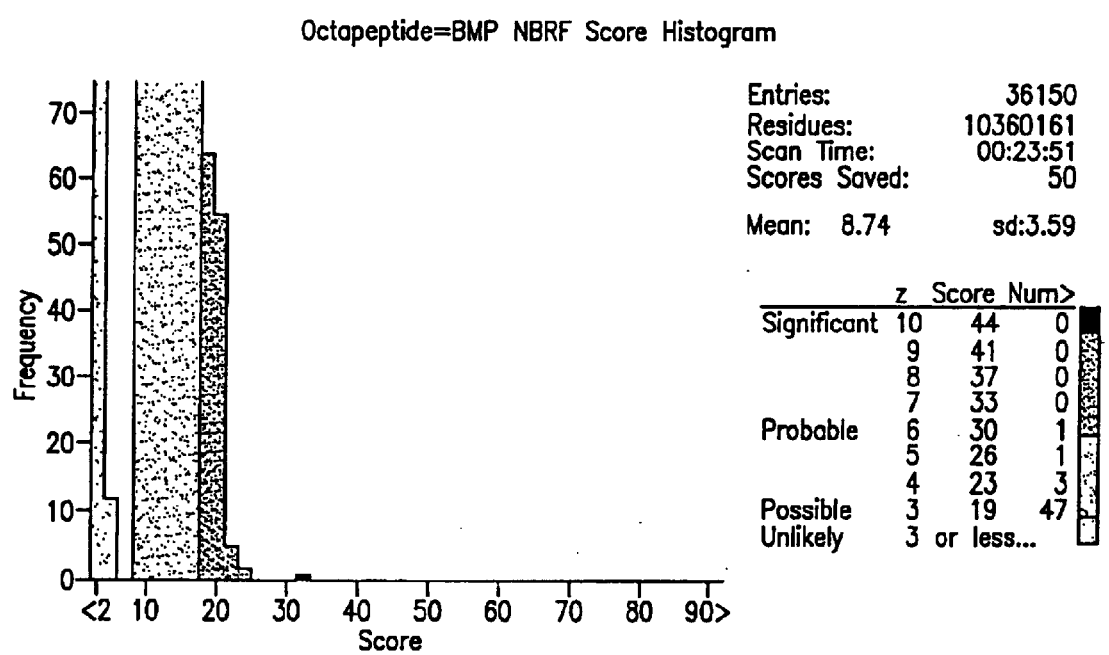
FIG. 2 shows an NBRF score histogram for BMP.
Figure 3:
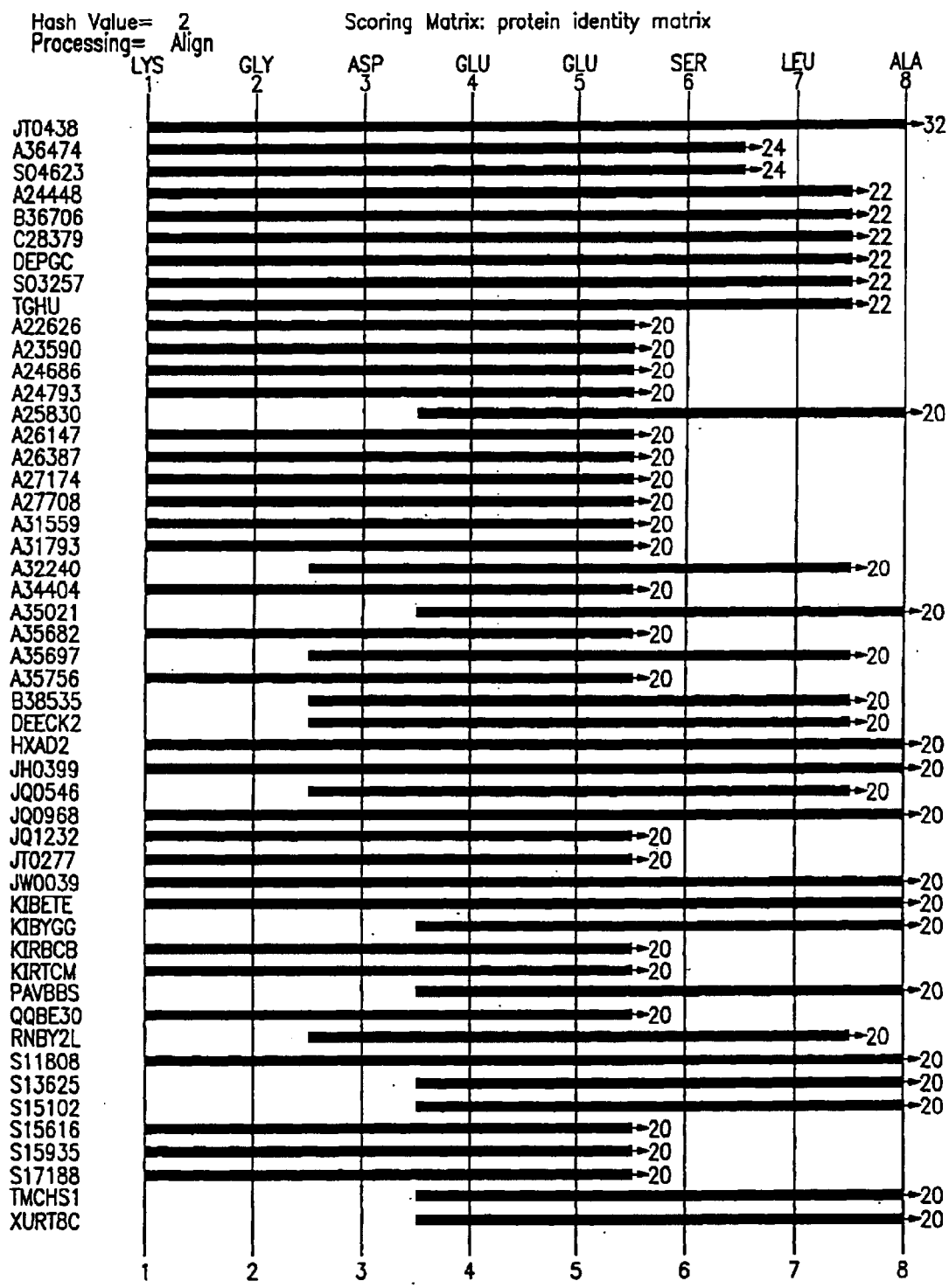
FIG. 3 is an NBRF horizontal map for a BMP protein identity matrix. The alphanumeric sequence in the left most column corresponds to the NBRF reference identification number. A list of the NBRF references is included in a subsection of the References Cited section which precedes the claims and these references are hereby incorporated by reference.
Figure 5A:
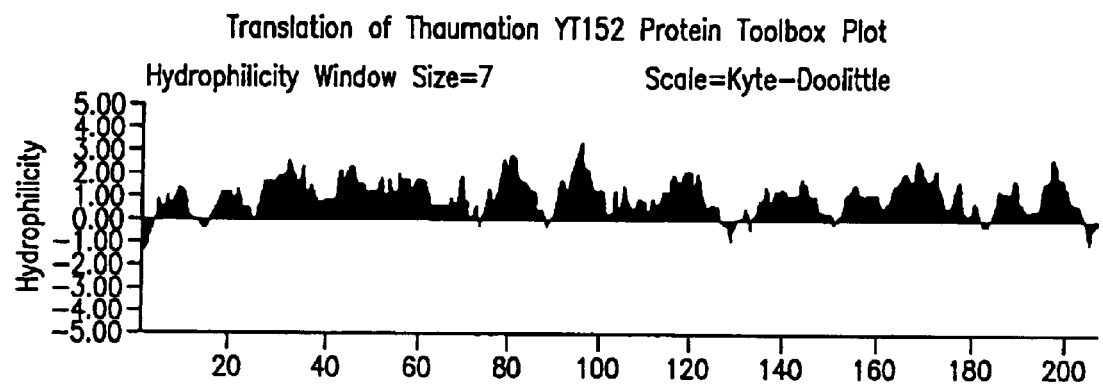
FIGS. 5(A)–(F) show various properties of native thaumatin.
Figure 5B:
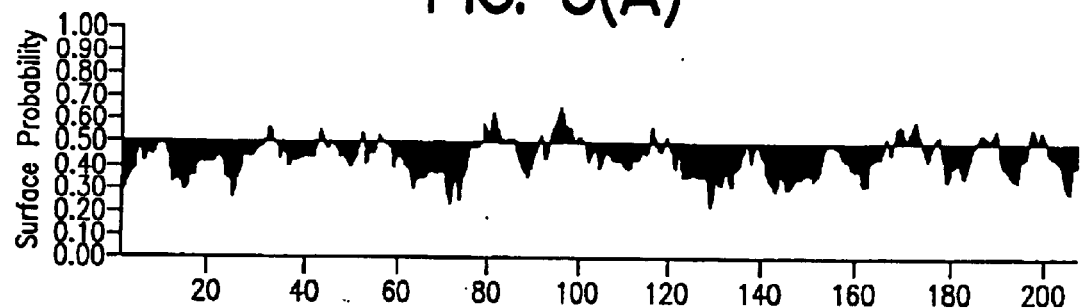
Figure 5C:
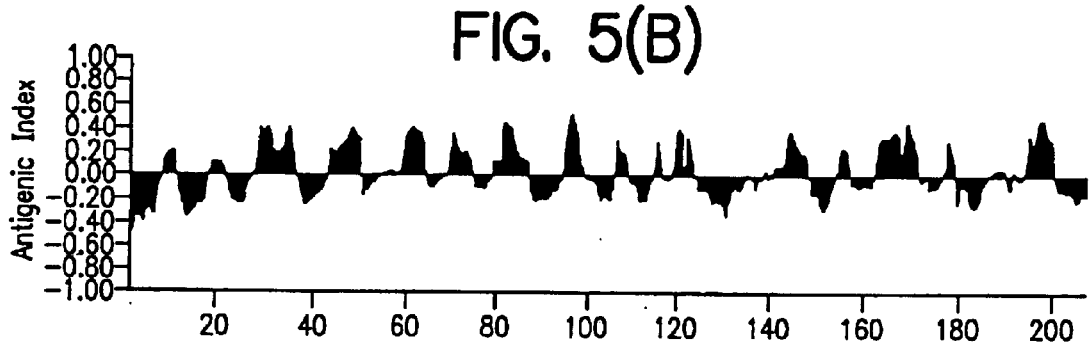
Figure 5D:
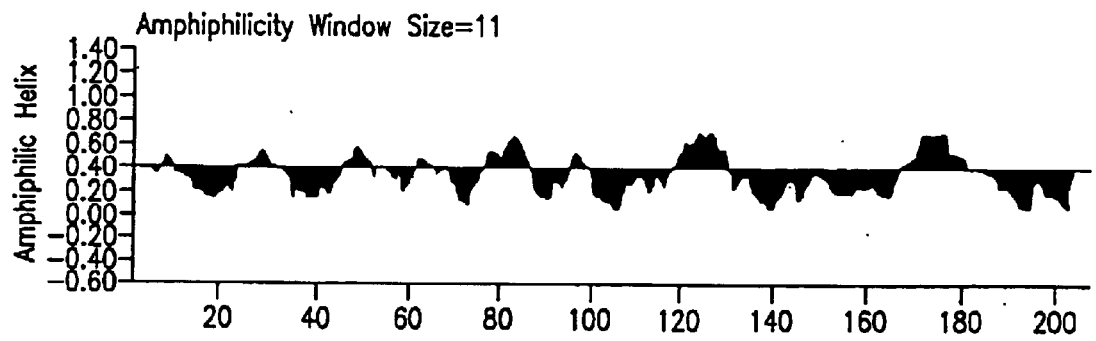
Figure 5E:
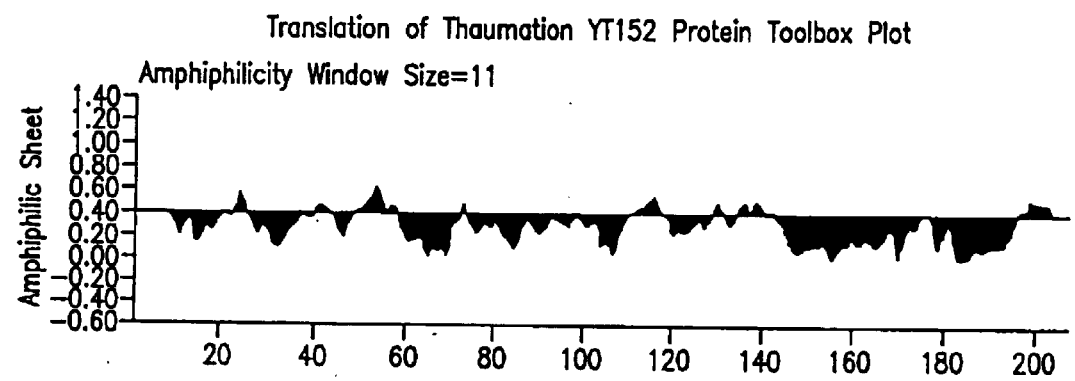
Figure 5F:
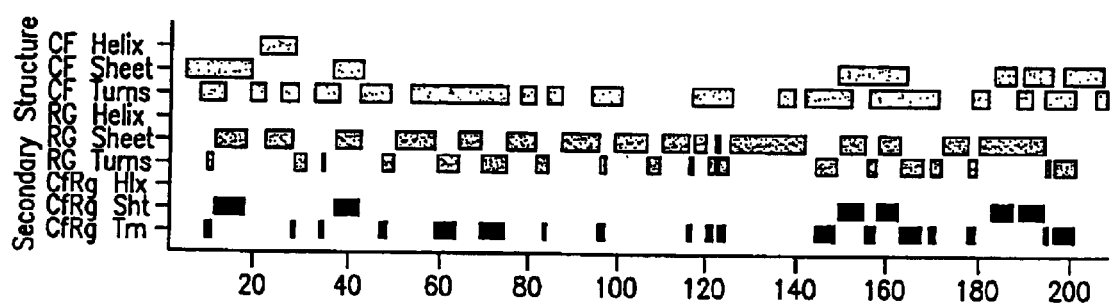
Figure 6A:
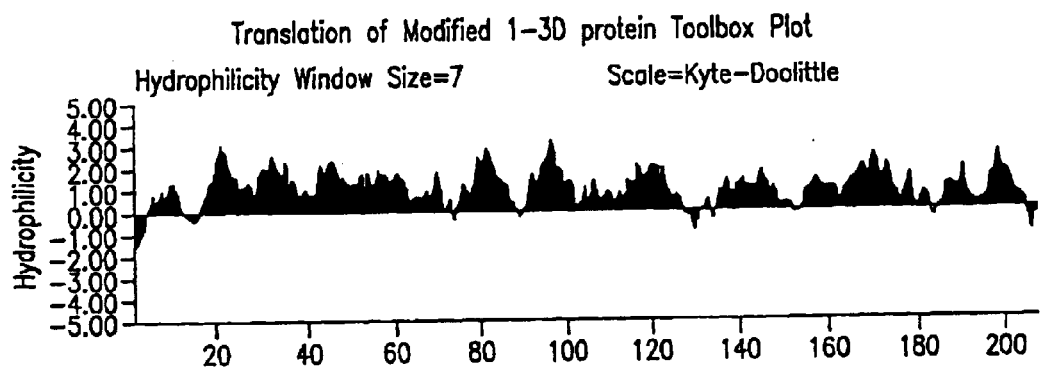
FIGS. 6(A)–(F) show various properties of modified thaumatin.
Figure 6B:
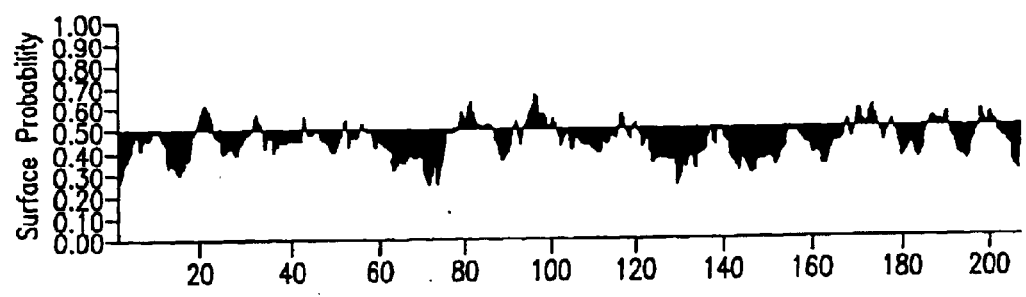
Figure 6C:
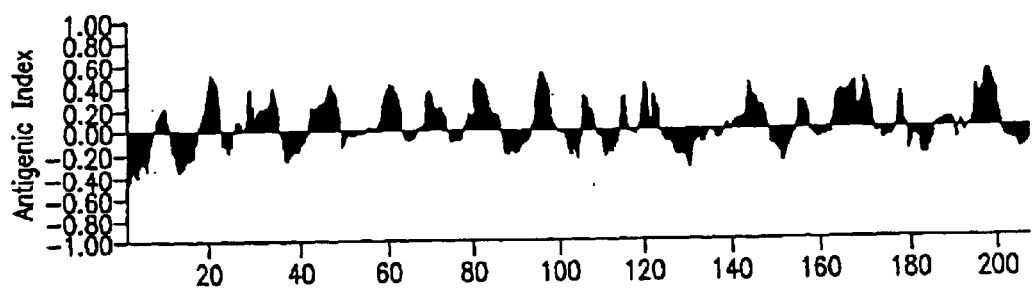
Figure 6D:
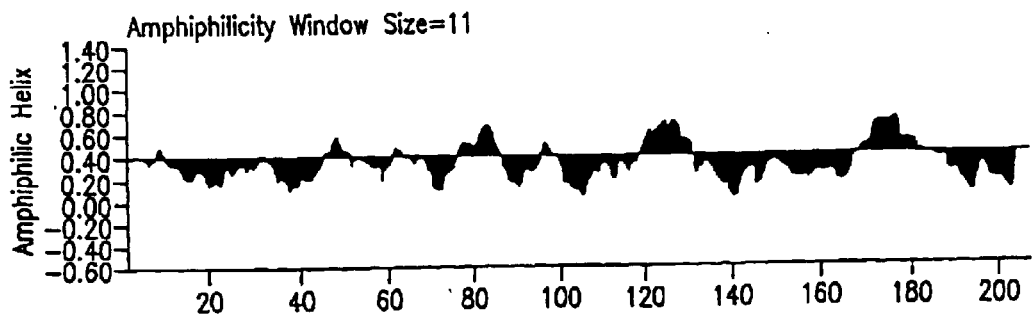
Figure 6E:
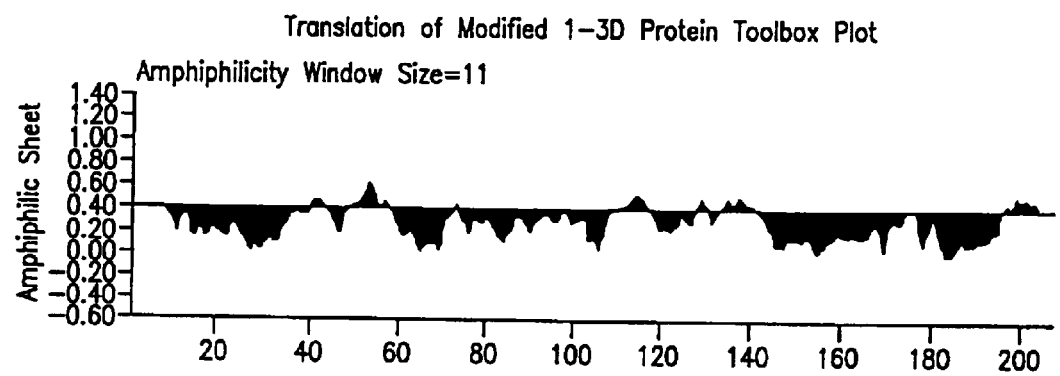
Figure 6F:
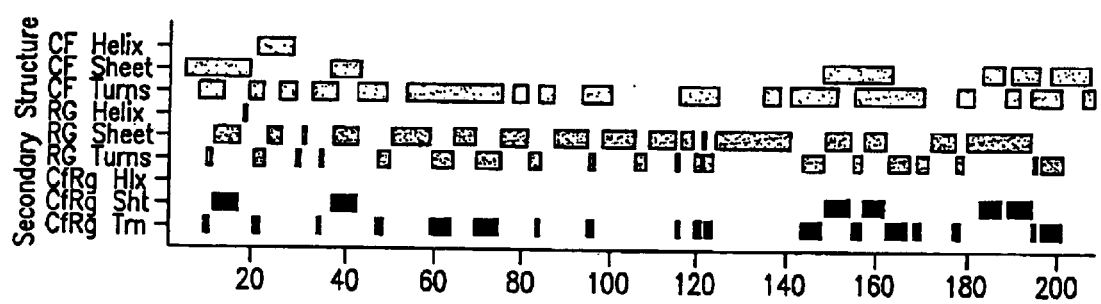

Thaumatin is a naturally occuring sweet-tasting peptide. Modified thaumatin is a thaumatin-like protein wherein more than one of the amino acids numbered 19–26 of thaumatin have been substituted, changed or modified. In particular, the amino acids numbered 19–26 of thaumatin are changed or modified to comprise amino acids having the flavorful or flavor enhancing amino acid region of another protein, polypeptide or peptide. In one embodiment, the change of as few as four amino acids in modified thaumatin provides significantly altered taste properties from thaumatin.

Monellin is a naturally occuring sweet-tasting peptide. Modified thaumatin is a monellin-like protein wherein more than one of the amino acids numbered 4–11 of monellin have been substituted, changed or modified. In particular, the amino acids numbered 4–11 of monellin are changed or modified to comprise amino acids having the flavorful or flavor enhancing amino acid region of another protein, polypeptide or peptide. In one embodiment, the change of as few as four amino acids in modified monellin provides significantly altered taste properties from monellin.

The octapeptide known as "delicious peptide" or "beefy meaty peptide" (BMP) is reported to enhance flavor and produces a umami and sour taste, especially in beef. BMP is an octapeptide that can be used in place of the active site of monellin or thaumatin to change or modify the flavor and flavor enhancing properties of these naturally sweet tasting proteins.

Derivatives of modified thaumatin and monellin can differ from modified thaumatin and monellin in amino acid sequence or in ways that do not involve sequence, or both. Derivatives in amino acid sequence are produced when one or more amino acids in naturally occurring thaumatin or monellin is substituted with a different natural amino acid, an amino acid derivative or non-native amino acid. Particularly preferred embodiments include naturally occurring thaumatin or monellin, or biologically active fragments of naturally occurring thaumatin or monellin, whose sequences differ from the wild type sequence by one or more conservative amino acid substitutions, which typically have minimal influence on the secondary structure and hydrophobic nature of the protein or peptide. Derivatives may also have sequences which differ by one or more non-conservative amino acid substitutions, deletions or insertions which do not abolish the thaumatin or monellin biological activity. Conservative substitutions (substituents) typically include the substitution of one amino acid for another with similar characteristics such as substitutions within the following groups: valine, glycine; glycine, alanine; valine, isoleucine; aspartic acid, glutamic acid; asparagine, glutamine; serine, threonine; lysine, arginine; and phenylalanine, tyrosine. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

Other conservative substitutions can be taken from Table 1, and yet others are described by Dayhoff in the Atlas of Protein Sequence and Structure (1988).

TABLE 1

Conservative Amino Acid Replacements

| For Amino Acid | Code | Replace with any of |
|---|---|---|
| Alanine | A | D-Ala, Gly, beta-ALa, L-Cys, D-Cys |
| Arginine | R | D-Arg, Lys, homo-Arg, D-homo-Arg, Met, D-Met, Ile, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |

TABLE 1-continued

Conservative Amino Acid Replacements

| For Amino Acid | Code | Replace with any of |
|---|---|---|
| Glycine | G | Ala, D-Ala, Pro, D-Pro, Beta-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val, Norleu |
| Phenylalanine | F | D-Phe, Tyr, D-Thr, L-Dopa, His, D-His, Trp, D-Trp, Trans 3,4 or 5-phenylproline, cis 3,4 or 5 phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), Val, D-Val |
| Threonine | T | D-Thr, Ser, D-Ser, allo-Thr, Met, D-Met, Met(O) D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other derivatives within the invention are those with modifications which increase peptide stability. Such derivatives may contain, for example, one or more non-peptide bonds (which replace the peptide bonds) in the peptide sequence. Also included are: derivatives that include residues other than naturally occurring L-amino acids, such as D-amino acids or non-naturally occurring or synthetic amino acids such as beta or gamma amino acids and cyclic derivatives. Incorporation of D- instead of L-amino acids into the polypeptide may increase its resistance to proteases. See, e.g., U.S. Pat. No. 5,219,990, incorporated by reference herein.

The polypeptides of this invention may also be modified by various changes such as insertions, deletions and substitutions, either conservative or nonconservative where such changes might provide for certain advantages in their use.

In other embodiments, derivatives with amino acid substitutions which are less conservative may also result in desired derivatives, e.g., by causing changes in charge, conformation and other biological properties. Such substitutions would include for example, substitution of hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

Derivatives within the scope of the invention include proteins and peptides with amino acid sequences having at least eighty percent homology with thaumatin or monellin. More preferably the sequence homology is at least ninety percent, or at least ninety-five percent.

Just as it is possible to replace substituents of the scaffold, it is also possible to substitute functional groups which decorate the scaffold with groups characterized by similar features. These substitutions will initially be conservative, i.e., the replacement group will have approximately the same size, shape, hydrophobicity and charge as the original group. Non-sequence modifications may include, for example, in vivo or in vitro chemical derivatization of portions of naturally occurring thaumatin or monellin, as well as changes in acetylation, methylation, phosphorylation, carboxylation or glycosylation.

In a further embodiment the protein is modified by chemical modifications in which activity is preserved. For example, the proteins may be amidated, sulfated, singly or multiply halogenated, alkylated, carboxylated, or phosphorylated. The protein may also be singly or multiply acylated, such as with an acetyl group, with a farnesyl moiety, or with a fatty acid, which may be saturated, monounsaturated or polyunsaturated. The fatty acid may also be singly or multiply fluorinated. The invention also includes methionine analogs of the protein, for example the methionine sulfone and methionine sulfoxide analogs. The invention also includes salts of the proteins, such as ammonium salts, including alkyl or aryl ammonium salts, sulfate, hydrogen sulfate, phosphate, hydrogen phosphate, dihydrogen phosphate, thiosulfate, carbonate, bicarbonate, benzoate, sulfonate, thiosulfonate, mesylate, ethyl sulfonate and benzensulfonate salts.

Derivatives of thaumatin or monellin may also include peptidomimetics of thaumatin or monellin. Such compounds are well known to those of skill in the art and are produced through the substitution of certain R groups or amino acids in the protein with non-physiological, non-natural replacements. Such substitutions may increase the stability of such compound beyond that of the naturally occurring compound.

It will be appreciated from the present disclosure that modified thaumatin, modified monellin and their derivatives according to the present invention can be used to alter, vary, fortify modify, enhance or otherwise improve the taste of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify its organoleptic character.

The term "enhance" is intended herein to mean the intensification (by the use of the modified thaumatin or modified monellin and derivatives of the present invention) of a flavor or aroma note or nuance in a foodstuff or dairy product or cheese without changing the quality of said note or nuance.

The term "flavoring composition" is taken to mean one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible materials for man or animals which materials usually do, but need not, have nutritional value. Thus, foodstuffs include meats, gravies, soups, convenience foods, malt, alcoholic, milk and dairy products, seafoods, candies, vegetables, animal foods, veterinary products and the like.

The modified proteins and derivatives of the present invention can be combined with conventional flavoring agents or adjuvants. Such co-ingredients or flavor adjuvants are well known in the art for such and have been extensively described in the literature. Requirements of such adjuvants are: (1) that they be non-reactive with the carboxylic acid mixture of the present invention; (2) that they be organoleptically compatible with the mixture of the present invention such that the flavor of the mixture is not adversely affected by the use of the adjuvant; and (3) that they be ingestibly acceptable and thus non-toxic or otherwise non-deleterious. Apart from these requirements, conventional materials can be used and broadly include other flavor materials, vehicles, stabilizers, thickeners, surface active agents, conditioners, and flavor intensifiers.

The following terms are used in accordance with their meanings in the art. DNA is deoxyribonucleic acid whether single- or double-stranded. Complementary DNA (cDNA) is DNA which has a nucleic acid sequence obtained from reverse transcription of messenger ribonucleic acid (mRNA). Recombinant genetic expression refers to the methods by which a nucleic acid molecule encoding a polypeptide of interest is used to transform a host cell so that the host cell will express the polypeptide of interest. A plasmid or vector can be used to introduce a nucleic acid molecule into a host cell. A plasmid or vector can comprise, but need not, in addition to the gene or nucleic acid sequence of interest, a gene that expresses a selectable marker or phenotype and a gene that can control (induce or inhibit) the expression of the gene of interest under certain conditions.

Recombination Methods

Recombinant expression vectors containing a nucleic acid sequence encoding modified thaumatin or modified monellin can be prepared using well known methods. The expression vectors include a modified thaumatin or modified monellin DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the modified thaumatin or modified monellin DNA sequence. Thus, a promoter nucleotide sequence is operably linked to a modified thaumatin or modified monellin DNA sequence if the promoter nucleotide sequence controls the transcription of the modified thaumatin or modified monellin DNA sequence. The ability to replicate in the desired host cells, usually conferred by an origin of replication, and a selection gene by which transformants are identified, may additionally be incorporated into the expression vector.

In addition, sequences encoding appropriate signal peptides that are not naturally associated with modified thaumatin or modified monellin can be incorporated into expression vectors. For example, a DNA sequence for a signal peptide (secretory leader) may be fused in-frame to the modified thaumatin or modified monellin sequence so that modified thaumatin or modified monellin is initially translated as a fusion protein comprising the signal peptide. A signal peptide that is functional in the intended host cells enhances extracellular secretion of the modified thaumatin or modified monellin polypeptide. The signal peptide may be cleaved from the modified thaumatin or modified monellin polypeptide upon secretion of modified thaumatin or modified monellin from the cell.

Suitable host cells for expression of modified thaumatin or modified monellin polypeptides include prokaryotes, yeast or higher eukaryotic cells. Appropriate cloning and expression vectors for use with bacterial, fungal, yeast, and mammalian cellular hosts are described, for example, in Pouwels et al. Cloning Vectors: A Laboratory Manual, Elsevier, N.Y., (1985). Cell-free translation systems could also be employed to produce modified thaumatin or modified monellin polypeptides using RNAs derived from DNA constructs disclosed herein.

Prokaryotes include gram negative or gram positive organisms, for example, *E. coli* or *Bacilli*. Suitable prokaryotic host cells for transformation include, for example, *E. coli, Bacillus subtilis, Salmonella typhimurium*, and various other species within the genera *Pseudomonas, Streptomyces*, and *Staphylococcus*.

In a prokaryotic host cell, such as *E. coli*, a modified thaumatin or modified monellin polypeptide may include an N-terminal methionine residue to facilitate expression of the recombinant polypeptide in the prokaryotic host cell. The N-terminal Met may be cleaved from the expressed recombinant modified thaumatin or modified monellin polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a modified thaumatin or modified monellin DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include .beta.-lactamase (penicillinase), lactose promoter system (Chang et al., Nature 275:615, 1978; and Goeddel et al., Nature 281:544, 1979), tryptopban (trp) promoter system (Goeddel et al., Nucl. Acids Res. 8:4057, 1980; and EP-A-36776) and tac promoter (Maniatis, Molecular Cloning: A Laboratory Manual, Cold Spring Harbor Laboratory, p. 412, 1982). A particularly useful prokaryotic host cell expression system employs a phage .lambda.P.sub.L promoter and a cI857ts thermolabile repressor sequence. Plasmid vectors available from the American Type Culture Collection which incorporate derivatives of the .lambda.P.sub.L promoter include plasmid pHUB2 (resident in *E. coli* strain JMB9 (ATCC 37092)) and pPLc28 (resident in *E. coli* RR1 (ATCC 53082)).

Modified thaumatin or modified monellin polypeptides alternatively may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2.mu. yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, 1980) or other glycolytic enzymes (Hess et al., j. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., Gene, 107:285–195 (1991); and van den Berg et. al., Bio/Technology, 8:135–139 (1990). Another alternative is the glucose-repressible ADH2 promoter described by Russell et al. (J. Biol. Chem. 258:2674, 1982) and Beier et al. (Nature 300:724, 1982). Shuttle vectors replicable in both yeast and *E. coli* may be constructed by inserting DNA sequences from pBR322 for selection and replication in *E. coli* (Amp.sup.r gene and origin of replication) into the above-described yeast vectors.

The yeast .alpha.-factor leader sequence may be employed to direct secretion of a modified thaumatin or modified monellin polypeptide. The .alpha.-factor leader sequence is often inserted between the promoter sequence and the structural gene sequence. See, e.g., Kurjan et al., Cell 30:933, 1982; Bitter et al., Proc. Natl. Acad. Sci. USA 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929, 1978.

The Hinnen et al. protocol selects for Trp.sup.+ transformants in a selective medium, wherein the selective medium consists of 0.67% yeast nitrogen base, 0.5% casamino acids, 2% glucose, 10 .mu.g/ml adenine and 20 mu.g/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 .mu.g/ml adenine and 80.mu.g/ml uracil. Derepression of the ADH2 promoter occurs when glucose is exhausted from the medium.

Mammalian or insect host cell culture systems could also be employed to express recombinant modified thaumatin or modified monellin polypeptides. Baculovirus systems for production of heterologous proteins in insect cells are reviewed by Luckow and Summers, Bio/Technology 6:47 (1988). Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (EMBO J. 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., Nature 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, a heterologous signal sequence may be added, such as the signal sequence for IL-7 described in U.S. Pat. No. 4,965,195; the signal sequence for IL-2 receptor described in Cosman et al., Nature 312:768 (1984); the IL-4 signal peptide described in EP 367,566; the type I IL-1 receptor signal peptide described in U.S. Pat. No. 4,968,607; and the type II IL-1 receptor signal peptide described in EP 460,846.

An isolated and purified, modified thaumatin or modified monellin protein according to the invention may be produced by recombinant expression systems as described above or purified from naturally occurring cells. Modified thaumatin or modified monellin can be substantially purified, as indicated by a single protein band upon analysis by SDS-polyacrylamide gel electrophoresis (SDS-PAGE). One process for producing modified thaumatin or modified monellin comprises culturing a host cell transformed with an expression vector comprising a DNA sequence that encodes modified thaumatin or modified monellin under conditions sufficient to promote expression of modified thaumatin or modified monellin. Modified thaumatin or modified monellin is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium. For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify modified thaumatin or modified monellin. Some or all of the foregoing purification steps, in various combinations, are well known and can be employed to provide an isolated and purified recombinant protein.

It is possible to utilize an affinity column comprising a modified thaumatin or modified monellin-binding protein to affinity-purify expressed modified thaumatin or modified monellin polypeptides. Modified thaumatin or modified monellin polypeptides can be removed from an affinity column using conventional techniques, e.g., in a high salt elution buffer and then dialyzed into a lower salt buffer for use or by changing pH or other components depending on the affinity matrix utilized.

Recombinant protein produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells can be employed to express modified thaumatin or modified monellin as a secreted polypeptide in order to simplify purification. Secreted recombinant polypeptide from a yeast host cell fermentation can be purified by methods analogous to those disclosed by Urdal et al. (J. Chromatog. 296:171, 1984). Urdal et al. describe two sequential, reversed-phase HPLC steps for purification of recombinant human IL-2 on a preparative HPLC column.

Antisense or sense oligonucleotides comprising a single-stranded nucleic acid sequence (either RNA or DNA) capable of binding to a target modified thaumatin or modified monellin mRNA sequence (forming a duplex) or to the modified thaumatin or modified monellin sequence in the double-stranded DNA helix (forming a triple helix) can be made according to the invention. Antisense or sense oligonucleotides, according to the present invention, comprise a fragment of the coding region of modified thaumatin or modified monellin cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, Cancer Res. 48:2659, 1988 and van der Krol et al., BioTechniques 6:958, 1988.

Binding of antisense or sense oligonucleotides to target nucleic acid sequences results in the formation of complexes that block translation (RNA) or transcription (DNA) by one of several means, including enhanced degradation of the duplexes, premature termination of transcription or translation, or by other means. The antisense oligonucleotides thus may be used to block expression of modified thaumatin or modified monellin proteins.

Antisense or sense oligonucleotides further comprise oligo-nucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, CaPO.sub.4-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other §cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

A preferred recombinant expression system is the *Pichia pastoris* expression system. The yeast *Pichia pastoris*, a microbial eukaryote, has been developed into an expression system. As a yeast, *Pichia pastoris* is as easy to use as *E. coli*, while having the advantages of eukaryotic expression (e.g. protein processing, folding, and posttranslational modifications). While possessing these advantages, it is faster, easier, and cheaper to use than other eukaryotic expression systems, such as baculovirus or mammalian tissue culture, and generally gives higher expression levels. *P. pastoris* is similar to the baker's yeast, *Saccharomyces cerevisiae,* including having the advantages of molecular and genetic manipulations, but with the added advantages of 10- to 100-fold higher heterologous protein expression levels and the protein processing characteristics of higher eukaryotes.

*Pichia pastoris* is completely amenable to the genetic, biochemical, and molecular biological techniques that have been developed over the past several decades for *S. cerevisiae* with little or no modification. In particular, transformation by complementation, gene disruption and gene replacement techniquest developed for *S. cerevisiae* work equally well for *Pichia pastoris.*

The genetic nomenclature adopted for *Pichia pastoris* mirrors that used for *S. cerevisiae* (unlike that of *Sc. pombe*). For example, the gene from *S. cerevisiae* that encodes the enzyme histidinol dehydrogenase is called the HIS4 gene and likewise the homologous gene from *Pichia pastoris* that encodes the same enzyme is called the *Pichia pastoris* HIS4 gene, and so on. there is a very high degree of cross-functionality between *Pichia pastoris* and *S. cerevisiae.* For instance, many *S. cerevisiae* genes have been shown to genetically complement the comparable mutants in *Pichia pastoris,* and vice versa (e.g. the *Pichia pastoris* HIS4 gene functionally complements *S. cerevisiae* his4 mutants and the *S. cerevisiae* HIS4 gene functionally complements *Pichia pastoris* his4 mutants; other cross-complementing genes that have been identified include LEU2, ARG4, TRP1, and URA3).

*Pichia pastoris* as a Methylotropic Yeast

*Pichia pastoris,* representing one of four different genera of methylotropic yeasts, which also include *Candida, Hansenula,* and *Torulopsis,* is capable of metabolizing methanol as a sole carbon source. The first step in the metabolism of methanol is the oxidation of methanol to formaldehyde by the enzyme alcoholoxidase. Expression of this enzyme, coded for by the AOX1 gene, is tightly regulated and induced by methanol to very high levels, typically $\geq 30\%$ of the total soluble protein in cells grown with methanol as the carbon source. The AOX1 gene has been isolated and a plasmid-borne version of the AOX1 promoter is used to drive expression of the gene of interest for heterologous protein expression.

Expression of the AOX1 gene is controlled at the level of transcription. IN methanol grown cells approximately 5% of the polyA+ RNA is from the AOX1 gene. The regulation of the AOX1 gene is similar to the regulation of the GAL1 gene (and others) of *S. cerevisiae* in that control involves both a repression/derepression mechanism. However, unlike the situation in *S. cerevisiae,* derepression alone of the AOX1 gene (i.e. absence of a repressing carbon source such as glucose) is not sufficient to generate even minute levels of expression from the AOX1 gene. The inducer, methanol, is necessary for expression.

Use for Heterologous Protein Expression

*Pichia pastoris* has been used successfully to express a wide range of heterologous proteins. Heterologous expression in *Pichia pastoris* can be either intracellular or secreted. Secretion requires the presence of a signal sequence on the expressed protein to target it to the secretory pathway. While several different secretion signal sequences have been used successfully, including the native secretion signal present on some heterologous proteins, success has been variable. To improve the chances for success, two different vectors with different secretion signals are included in this kit: The vector, pHIL-S1, carries a native *Pichia pastoris* signal from the acid phosphatase gene, PHOL. The vector, pPIC9, carries the secretion signal from the *S. cerevisiae* mating factor pre-pro peptide.

Another advantage of expressing secreted proteins is that *Pichia pastoris* secretes very low levels of native proteins. that, combined with the very low amount of protein in the *Pichia* growth media, means that the secreted heterologous protein comprises the vast majority of the total protein in the media and serves as the first step in purification of the protein.

Like *S. cerevisiae,* linear DNA can generate stable transformants of *Pichia pastoris* via homologous recombination between the transforming DNA and regions of homology within the genome. Such integrants show extreme stability in the absence of selective pressure even when present as multiple copies.

The expression vectors included int his kit carry the HIS4 gene for selection and are designed to be linearized with a restriction enzyme such that HIS$^+$ recombinants can be generated by integration at the his4 locus (a non-deletion, very low spontaneous reversion mutation) or at the AOX1 locus. Integration events at the AOX1 locus can result in the complete removal of the AOX1 coding region (i.e. gene replacement) that in turn results in a recombinant phenotype of His$^+$ Mut$^-$ (Mut$^-$ refers to the methanol utilization minus phenotype caused by the loss of alcohol oxidase activity encoded by the AOX1 gene that results in a no growth or slow growth phenotype on methanol media). His$^+$ transformants can be readily and easily screened for the Mut$^-$ phenotype, indicating integration at the AOX1 locus. The His$^+$ Mut$^-$ clones can be further screened for expression of the heterologous protein of interest.

A number of independently isolated His$^+$ Mut$^-$ recombinants are routinely screened for expression of the heterologous protein of interest because of the observation of clonal variation (or difference in levels of expressing heterologous protein seen among different transformants with the same phenotype (His$^+$ Mut$^-$)). In some cases this clonal variation can be explained by a difference in the number of copies of the integrated plasmid (i.e. more copies=more expressed protein), but it is not simply copy number that determines protein expression level. There are several examples where one or more copies of the integrants express at the same level (and that level is high), as well as examples where an increase in the integrant copy number causes a decrease in the protein expression level. The best method at this time is to identify a successfully expressing clone among several (e.g. 10–20) His$^+$ Mut$^-$ transformants empirically.

Some examples of heterologous protein expression include:

TABLE 2

| Protein | Expression (g/L) | Where Expressed | Reference |
|---|---|---|---|
| Human serum albumin (HSA) | 4.0 | S | Barr, et al (1992) |
| β-galactosidase | 20,000 (U/mg total protein) | I | Tschopp, et al (1987a) |
| Hepatitis B surface antigen (HBSAg) | 0.4 | I | Cregg, et al (1987) |
| Tumor Necrosis Factor (TNF) | 10.0 | I | Sreekrishna, et al (1988) |
| Invertase | 2.3 | S | Tschopp, et al (1987b) |
| Bovine lysozyme c2 | 0.55 | S | Digan, et al (1989) |
| Tetanus toxin fragment C | 12.0 | I | Clare, et al (1991a) |
| Pertusis antigen P69 | 3.0 | I | Romanus, et al (1991) |
| Streptokinase (active) | 0.08 | I | Hagenson, et al (1989) |
| Human EGF | 0.5 | S | Cregg, et al (1993) |
| Mouse EGF | 0.45 | S | Claire, et al (1991b) |
| Aprotinin | 0.8 | S | Vedvick, et al (1991) |
| Kunitz protease inhibitor | 1.0 | S | Wagner, et al (1992) |

(S = secreted; I = intracellular)

Specifically, the invention provides a modified thaumatin protein having a modified amino acid sequence of amino acids 19 to 26 selected from an amino acid sequence differing from amino acids 19 to 26 of thaumatin (SEQ ID NO:2) by at least four amino acids; an amino acid sequence of beefy meaty peptide (SEQ ID NO:6); and an amino acid sequence of amino acids 4 to 11 of monellin (SEQ ID NO:4), derivatives of these proteins and nucleic acid sequence encoding their expression.

It also provides a modified monellin protein having a modified amino acid sequence of amino acids 4 to 11 selected from an amino acid sequence differing from amino acids 4 to 11 of monellin (SEQ ID NO:4) by at least four amino acids; an amino acid sequence of beefy meaty peptide (SEQ ID NO:6); and an amino acid sequence of amino acids 19 to 26 of thaumatin (SEQ ID NO:2), derivatives of these proteins and nucleic acids encoding their expression.

This invention provides antibodies to modified thaumatin. In a preferred embodiment the antibodies are monoclonal.

The invention provides vectors capable of expressing the modified thaumatin or the modified monellin in a transformed host cell. In a preferred embodiment, the vector is pPIC9. A preferred host cell is *Pichia pastoris*. Methods for performing the transformation are also provided as are methods of culturing the host cells and recovering the expressed proteins.

This invention will be better understood from the Examples which follow. However, one skilled in the art will readily appreciate that the specific methods and results discussed are merely illustrative of the invention as described more fully in the claims which follow thereafter.

EXAMPLES

Homology Search

An amino acid sequence homology search was conducted to identify regions of similarity among taste active proteins.

Specifically, homology searches were conducted using the eight residue sequences that show substantial relatedness in thaumatin, monellin 1 and the synthetic octapeptide BMP or delicious peptide. Gurmarin, miraculin, curculin and mabinlin (all sweet proteins) sequences were searched with broad criteria allowing 6 out of 8 mismatches and 2 offsets. The results indicated only weak homology, usually 2 of 8 and sometimes 3 of 8 mismatches. However, "monellin and thaumatin are the only two proteins known to have a very high specificity for the human sweet taste receptor." (Murzin, A. G. 1993)

Efforts to identify the active sites for sweetness of thaumatin and monellin have not been successful. Approaches involved searches for related amino acid sequences, immunological cross reactivity studies, comparisons of x-ray crystallographic 3-dimensional structures, modified protein studies and peptide fragment evaluations. Studies in which the active site for sweetness was sought by evaluating fragments of monellin and thaumatin were largely unsuccessful. Sweetness was not detected in monellin fragments and only in a very large fragment of thaumatin (about half of the molecule equivalent to 12 kDa) suggesting that tertiary structure is essential to produce sweetness. Similarly, attempts to identify the active site by chemical modification of certain amino acids of native monellin and thaumatin have not yielded a clear picture (although certain amino acids appear to be involved) due to conformational changes that likely occur. Recognizing the importance of tertiary structure, Kohmura et al. (1992) took the approach of conservatively modifying monellin to determine whether any of the aspartic acid (Asp) residues play a critical role in sweetness. Aspartic acid was replaced with either asparagine of L-aminobutyric acid which they believed would maintain the original tertiary structure. Only replacement of the Asp at position 7 in the B chain resulted in the loss of sweetness and suggests this is the most likely active site. This site is on the surface of the molecule and is distant from the sequence (B chain, amino acids 4 to 11) showing homology to thaumatin and synthetic octapeptide BMP.

As of the homology search, a review of the literature did not indicate that the region of interest in thaumatin (amino acids 19–26) were a region of particular interest with regard to sweetness or taste properties. Antibodies to monellin and thaumatin cross-react which indicates a high specificity for at least one epitope. An epitope can be defined by as few as three amino acids. While this region only has two amino acids in common for thaumatin and monellin, the overall conformation may be one that defines an antibody site. Also, the N-terminal region in thaumatin has been shown to affect the expression of sweetness where thaumatin has been recombinantly expressed in other organisms. It was observed that when thaumatin is compared to other thaumatin like proteins, the region of homology to BMP and monellin is the region of greatest dissimilarity. (Verrips, C. T. 1992, pp. 226–227).

Octapeptide Homology Comparison

A search for sequences similar to BMP and and a region monellin I was conducted against other "chemosensory" proteins, i.e. curculin, miraculin, gurmarin and thaumatin. While the exact homology was not identified, a region in the early part of thaumatin sequence overlapped with the region of interest and BMP and had an equivalent degree of homology. See FIG. 1. Cagan (1984) thought this homology was not significant, but noted that antibodies to thaumatin cross reacts with monellin and predicted cross reactivity of an antimonellin antibody with BMP. BMP does not act as a sweetner but as a flavor enhancer. Thaumatin, in addition to providing sweetness, has taste enhancement or modification properties. Since homology does not occure among all sweet tasting proteins, it seems possible that this region may play a role in taste enhancement. On this basis, monellin could also have taste enhancement properties. Thus, this homology could be a primary determiner of taste enhancement in these proteins and other sweet tasting proteins without this homology would not have significant taste enhancement properties.

A search of the 1992 NBRF protein database for BMP related sequences showed only one of the fifty highest scores was significant and that was the original BMP sequence. Thus, this sequence appears to be unique. Other proteins showed extensive homologies and occurred in a wide variety of proteins. It is possible that this homology confers taste enhancement to these proteins.

Modification of Thaumatin

A region was identified in thaumatin (residues 19–26) and monellin (residues 4–11 in the A chain) that have 50% homology with each other and with the octapeptide variously known as "delicious peptide" or "beefy meaty peptide" (BMP). See SEQ ID NO:6. Modified thaumatin was produced wherein the region of amino acids 19–26 of thaumatin was modified to specify the sequence for the BMP octapeptide to determine whether this modification changes the taste qualities associated with thauznatin. A gene encoding the modified thaumatin was used to transform yeast and was expressed as a polypeptide to be tested for its effect on flavor perception.

This modified thaumatin was shown to yield a recombinant protein that is not sweet (500 ppm) but alters the salty and savory impression (10 ppm) of succinic acid and the impression of a salt enhancer (IFF #30) comprising L-arginine, ammonium chloride, tartaric acid, monopotassium glutamate and ribotide.

TABLE 3

Salt Enhancer IFF #30.

| IPC | Ingredient | % as consumed | Weight |
|---|---|---|---|
| 14886 | L-arginine Nat. "FLG" | 0.17 | 320.75 |
| 14279 | Ammonium Chloride | 0.2 | 377.36 |
| 200810 | Tartaric acid Nat PWD "FLG" | 0.08 | 37.74 |
|  | Monopotassium glutamate | 0.13 | 245.28 |
| 183920 | Ribotide | 0.01 | 18.87 |
|  | Total | 0.59 | 1000.00 |

Suggested Usage: 0.02% as consumed.

TABLE 4

Amino Acid Composition of Modified Thaumatin

|  | No. | Percent |
|---|---|---|
| Non-polar: |  |  |
| A | 14 | 6.76 |
| V | 10 | 4.83 |
| L | 9 | 4.35 |
| I | 8 | 3.86 |
| P | 12 | 5.80 |
| M | 1 | 0.48 |
| F | 11 | 5.31 |
| W | 3 | 1.45 |
| Polar: |  |  |
| G | 24 | 11.59 |
| S | 15 | 7.25 |
| T | 20 | 9.66 |
| C | 16 | 7.73 |
| Y | 8 | 3.86 |
| N | 8 | 3.86 |
| Q | 4 | 1.93 |
| Acidic: |  |  |
| D | 8 | 6.28 |
| E | 13 | 3.86 |
| Basic: |  |  |
| K | 0 | 5.31 |
| R | 12 | 5.80 |
| H | 11 | 0.00 |

The calculated molecular weight of modified thaumatin is 22,292.

For comparison, native thaumatin has the following amino acid composition:

TABLE 5

Amino Acid Composition of Thaumatin

|  | No. | Percent |
|---|---|---|
| Non-polar: |  |  |
| A | 16 | 7.73 |
| V | 10 | 4.83 |
| L | 9 | 4.35 |
| I | 8 | 3.86 |
| P | 12 | 5.80 |
| M | 1 | 0.48 |
| F | 11 | 5.31 |
| W | 3 | 1.45 |
| Polar: |  |  |
| G | 24 | 11.59 |
| S | 14 | 6.76 |
| T | 20 | 9.66 |

TABLE 5-continued

Amino Acid Composition of Thaumatin

| | No. | Percent |
|---|---|---|
| C | 16 | 7.73 |
| Y | 8 | 3.86 |
| N | 8 | 3.86 |
| Q | 4 | 1.93 |
| Acidic: | | |
| D | 14 | 6.76 |
| E | 6 | 2.90 |
| Basic: | | |
| K | 11 | 5.31 |
| R | 12 | 5.80 |
| H | 0 | 0.00 |

Thaumatin has a calculated molecular weight of 22204.

References Cited

1. Cagan, R. H. (1984) "Peptide Interactions with Taste Receptors: Overlap in Taste Receptor Specificity." *Experientia* 40:843–844.
2. de Vos, A. M. et al. (1985) "Three Dimensional Structure of Thaumatin I, an Intensely Sweet Protein." *PNAS USA* 82:1406–1409.
3. Iijima, H. (1995) "Design and Protein Engineering of a Single-Chain Monellin." *Baiosaiensu to Indasutori* 53:963–966.
4. Iyengar, R. B. (1979) "The Complete Amino Acid Sequence of the Sweet Protein Thaumatin I." *Eur. J. Biochem.* 96:193–204.
5. Kim et al. U.S. Pat. No. 5,670,339.
6. Kohmura, M. et al. (1993) "The Sweetness Determinant Site of the Sweet Protein Monellin." *Pept. Chem. 1992, Proc. Jpn. Symp. 2d* 341–342.
7. Kuramitsu, R. et al. (1993) "New Usage of Aspartic Acid and Glutamic Acid as Food Materials." Chapter 10. NEED BOOK TITLE, PUBLISHER AND PAGES.
8. Murzin, A. G. (1993). *J.Mol. Biol.* 230:289.
9. Slootstra, J. W. et al. (1995) "Possible Active Site of the Sweet-tasting Protein Thaumatin." *Chemical Senses* 20:535–543.
10. Staff Report. (January 1996) "Thaumatin-The Sweetest Substance Known to Man Has a Wide range of Food Applications." *Food Technology* 74–75.
11. Suami, T. et al. (1996) "Molecular Mechanisms of Sweet Taste. Part 6: The Sweet Protein Monellin." *Food Chemistry* 56:275–281.
12. Tamura, M. T. et al. (1989) "The Relationship Between Taste and Primary Structure of 'Delicious Peptide.' LYS-GLY-ASP-GLU-GLU-SER-LEU-ALA from Beef Soup." *Agric. Biol. Chem.* 53:319–325.
13. Verrips, C. T. (1992) "Structure and Protein Engineering of Thaumatin and other Sweet Proteins." *Plant Microb. Biotechnol. Res. Ser.* 1:219–234.
14. Witty, M. and Higginbotham, J. D. eds. (1994) *Thaumatin.* CRC Press, Ann Arbor, Mich. 204 pp.
15. Yamasaki, Y and Maekawa, K. (1978) "A Peptide With Delicious Taste." *Agric. Biol. Chem.* 42:1761–1765.

NBRF References Cited (for peptide homology comparison)

1. Aguilar O. M., et al (1987), Nitrogen fixation protein—Rhizobium meliloti, *J. Bacteriol,* 169:5393–5400, C28379NBRF;;
2. Akusjarvi G. et al. (1981), Hexon protein—Human adenovirus 2, *Nucleic Acids Res.,* 9:1–17, HXAD2BNRF;
3. Alestrom P. et al. (1981), Hexon protein—Human adenovirus 2, *Atlas* November 1982, HXAD2NBRF;
4. Alin P. et al. (1989), Gluthathione transferase 8, cytosolic—Rat, *Biochem. J.,* 261:531–439, XURT8CNBRF;
5. Allison L. A. et al. (1985), DNA-directed RNA polymerase II 215K polypeptide—Yeast (*Saccharomyces cerevisiae*), *Cell,* 42:599–610, RNBY2LNBRF;
6. Aoki I. et al. (1991), Eosinophil granule major basic protein 1 precursor—Guinea pig, *FEBS Lett.,* 279:330–334, S13625NBRF;
7. Aoki I. et al. (1991), Eosinophil granule major basic protein 2 precursor—Guinea pig, *FEBS Lett.,* 282:56–60, S15102NBRF;
8. Au-Young J. et al. (1990), Chitin synthase—Imperfect fungus (*Candida albicans*), *Mol. Microbiol.,* 4:197–207, S11808NBRF;
9. Baer R. et al. (1984), BRRF2 protein—Epstein-Barr virus (strain B95-8), *Nature,* 310:207–211, QQBE30NBRF;
10. Bankier A. T. et al. (1983), Thymidine kinase—Epstein-Barr virus (strain B95-8), *EMBO J.,* 5:1959–1966, KIBETENBRF;
11. Begg G. S., et al. (1978), Connective-tissue activating peptide III—Human, *Proc. Natl. Acad. Sci U.S. A. Biochemistry,* 80:765–769, TGHUNBRF;
12. Benfield P. A. et al. (1984), Creatine kinase M chain—Rat, *J. Biol. Chem.,* 259:14979–14984, KIRTCMNBRF;
13. Benfield P. A. et al. (1988), Creatine kinase (CK)—Rat, *Gene,* 63:227–243, JT0277NBRF;
14. Buskin J. N., et al. (1985), Creatine kinase M chain—Mouse, *J. Mol. Evol.,* 22:334–341, A23590NBRF;
15. Calabrese L., et al. (1989), Superoxide dismutase (Cu—Zn)—Blue shark, *FEBS Lett,* 50:49–52, S04623NBRF;
16. Citron B. A. et al. (1984), Galactokinase—Yeast (*Saccharomyces cerevisiae*), *J. Bacteriol.,* 158:269–278, KIBYGGNBRF;
17. Dawson P. A. et al. (1989), Oxysterol-binding protein—Rabbit, *J. Biol. Chem.,* 264:16798–16803, A34404NBRF;
18. Fang J. K., et al. (1980), 3-Hydroxyacyl—CoA dehydrogenase—Pig, submitted to the Atlas, October 1982, 116-196-198, DEPGCNBRF;
19. Ghosh S. et al. (1990), Transcription factor NF-kappaB—Mouse, *Cell,* 62:1019–1029, A35697NBRF;
20. Gitt M. A., et al. (1985), DNA-directed RNA polymerase sigma chain—*Bacillus subtilits, J. Biol. Chem,* 20:7178–7185, A22626NBRF;
21. Gustafson G. et al. (1989), Alpha-a protein—Barley stripe mosaic virus, *Virology,* 170:370–377, PAVBBSNBRF;
22. Haas R. C. et al. (1990), Creatine kinase precursor, sarcomere-specific, mitochondrial—Human, *J. Biol. Chem.,* 265:6921–6927, A35756NBRF;
23. Helfman D. M. et al. (1985), Tropomyosin 1, smooth muscle—Chicken, *J. Biol. Chem.,* 259:14136–14143, TMCHS1NBRF;
24. Herring B. P. et al. (1990), Myosin-light-chain kinase, skeletal muscle—Rabbit, *J. Biol. Chem.,* 265:1724–1730, A35021NBRF;
25. Hirsch-Behnam A. et al. (1990), Hypothetical protein E1—Human papillomavirus, *Virus Res.,* 18:81–98, S15616NBRF;
26. Holt J. C., et al. (1986), Platelet basic protein—Human, *Biochemistry,* 25:1988–1996, A24448NBRF;
27. Hossle J. P., et al. (1986), B-creatine kinase protein—Chicken, *Nucleic Acids Res.,* 14:1449–1463, A24793NBRF;

28. Hossle J. P., et al. (1988), Creatine kinase precursor, mitochondrial—Chicken (fragment), *Biochem. Biophys. Res. Commun.* 151:408–416; A27708NBRF;
29. Jofuku K. D. et al. (1989), Trypsin inhibitor KTi3+ (Kunitz)—Soybean, *Plant Cell*, 1:427–435, JQ0968NBRF;
30. Jornvall H. et al. (1981), Hexon protein—Human adenovirus 2, *J. Biol. Chem.*, 256:6181–6186, HXAD2NBRF;
31. Klein A., et al. (1988), Methyl coenzyme M reductase beta chain—Methanococcus voltai, submitted to the EMBL Data Library, S03257NBRF;
32. Larimer F. W. et al. (1989), rev1 protein—Yeast (*Saccharomyces cerevisiae*), *J. Bacteriol.*, 171-230-237, A32240NBRF;
33. Lehman L. J. et al. (1990), Dinitrogenase reductase—*Rhodospirillum rubrum*, *Gene*, 95:143–147, JW0039NBRF;
34. Levin D. E., et al. (1990), Protein kinase 1—Yeast, *Proc. Natl. Acad. Sci. U.S.A.*, 87:8272–8276, A36474NBRF;
35. Lin C. S., et al. (1988), L-plastin—Human, *Mol. Cell. Biol.* 8:4659–4668, A31559NBRF;
36. Mariman E. C. M. et al. (1989), Creatine kinase chain B—Human, *Nucleic Acids Res.*, 17–6385, S15935NBRF;
37. Mariman E. C. M., et al. (1987), Creatine kinase B chain—Human, *Genomics*, 1:126–137, A27174NBRF;
38. Michaels M. L. et al. (1990), Adenine glycosylase—*Escherichia coli*, *Nucleic Acids Res.*, 18:3841–3845, JQ0546BNRF;
39. Mukai H. et al. (1991), Calcineurin B-like protein—Rat, *Biochem. Biophys. Res. Commun.*, 179:1325–1330, JQ1232NBRF;
40. Nambu J. R., et al. (1986), Egg-laying hormone-1 precursor—Sea hare, *J. Neurosci*, 6:2026–2036, A26147NBRF;
41. Nishiya Y., et al. (1990), Neutral proteinase—*Bacillus stearothermophilus*, *J. Bacteriol*, 172:4861–4869, B36706NBRF;
42. Payne R. M. et al. (1991), Creatine kinase—Rat, *Biochem. Biophys. Acta*, 1089:352–361, S17188NBRF;
43. Pentecost B. T. et al. (1990), Creatine kinase B chain—Rat, *Mol. Endocrinol.*, 4:1000–1010, A35682NBRF;
44. Perryman M. B., et al. (1986), Creatine kinase M chain—Human, *Biochem. Biophys. Res. Commun.*, 140:981–989, A26387NBRF;
45. Pickering L. et al. (1985), Creatine kinase B chain—Rabbit, *Proc. Natl. Acad. Sci. U.S.A.*, 82:2310–2314, KIRBCBNRF;
46. Roman D., et al. (1985), Creatine Kinase M chain—Dog, *Proc. Natl. Acad. Sci U.S.A.*, 82:8394–8398, A24685NBRF;
47. Rupp F. et al. (1991), Agrin—Rat, *Neuron*, 6:811–823, JH0399BNRF;
48. Sanders C. et al. (1985), Tropomyosin 1, smooth muscle—Chicken, *J. Biol. Chem.*, 260:7264–7275, TMCHS1NBRF;
49. Takio K., et al. (1986), Myosin light chain kinase, skeletal muscle—Rabbit, *Biochemistry*, 25:8049–8057;
50. Tamura M., et al. (1989), Delicious peptide—Bovine, *Agric. Biol. Chem.*, 53:319–325, JT0438NBRF;
51. Trask R. V., et al. (1988), Creatine kinase M chain—Human, *J. Biol. Chem.*, $_2$63:17142–17149NBRF;
52. Tsai-Wu J. J. et al. (1991), MicA protein—*Escherichia coli*, *J. Bacteriol.*, 173:1902–1910, B38535NBRF; and
53. Zakin M. M., et al (1983), metL bifunctional enzyme—*Escherichia coli*, 258:3028–3031, DEECK2NBRF.

What is claimed is:

1. A nucleic acid molecule encoding a modified thaumatin protein of SEQ ID NO: 2, wherein amino acid residues 19 through 26 of the thaumatin protein of SEQ ID NO:2 are replaced by an amino acid sequence selected from the group consisting of an amino acid sequence of a beefy meaty peptide of SEQ ID NO:6 or an amino acid sequence of amino acid residues 4 through 11 of a monellin protein of SEQ ID NO:4.

2. The nucleic acid molecule of claim 1, wherein the nucleic acid is deoxyribonucleic acid.

3. The nucleic acid molecule of claim 2, wherein the molecule comprises SEQ ID NO:1.

4. A nucleic acid molecule encoding a modified monellin protein wherein amino acid residues 4 through 11 of the monellin protein of SEQ ID NO:4 are replaced by an amino acid sequence selected from the group consisting of an amino acid sequence that differs from the amino acid sequence of the monellin protein of SEQ ID NO: 4 by at least four amino acid residues, an amino acid sequence of a beefy meaty peptide of SEQ ID NO:6, or an amino acid sequence of amino acids 19 through 26 of a thaumatin protein of SEQ ID NO:2.

5. The nucleic acid molecule of claim 4, wherein the nucleic acid is deoxyribonucleic acid.

6. The nucleic acid molecule of claim 5, wherein the molecule comprises SEQ ID NO:3.

7. A vector expressing the modified thaumatin protein encoded by the nucleic acid molecule of claim 1 or the modified monellin protein encoded by the nucleic acid molecule of claim 4.

8. The vector of claim 7, wherein the vector is pPIC9.

9. A host cell transformed by the vector of claim 7.

10. The host cell of claim 9, wherein the host cell is *Pichia pastoris*.

11. A method of producing a host cell, wherein the host cell is transformed by the vector of claim 7.

12. A process for preparing a modified thaumatin protein or modified monellin protein comprising culturing the host cell of claim 9 under conditions promoting expression, and recovering the modified thaumatin protein or modified monellin protein from the culture medium.

* * * * *